United States Patent
Yamamoto et al.

(10) Patent No.: US 8,945,724 B2
(45) Date of Patent: Feb. 3, 2015

(54) NITROGEN-CONTAINING HETEROCYCLIC DERIVATIVE AND ORGANIC ELECTROLUMINESCENT DEVICE USING THE SAME

(75) Inventors: Hiroshi Yamamoto, Chiba (JP); Takashi Arakane, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 316 days.

(21) Appl. No.: 12/810,957

(22) PCT Filed: Dec. 24, 2008

(86) PCT No.: PCT/JP2008/073457
§ 371 (c)(1),
(2), (4) Date: Oct. 4, 2010

(87) PCT Pub. No.: WO2009/084543
PCT Pub. Date: Jul. 9, 2009

(65) Prior Publication Data
US 2011/0012092 A1    Jan. 20, 2011

(30) Foreign Application Priority Data
Dec. 27, 2007 (JP) ................................ 2007-337994
Dec. 27, 2007 (JP) ................................ 2007-337995

(51) Int. Cl.
*H01L 51/54* (2006.01)
*C09K 11/06* (2006.01)
(Continued)

(52) U.S. Cl.
CPC .............. *C09K 11/06* (2013.01); *C07D 235/08* (2013.01); *C07D 235/18* (2013.01);
(Continued)

(58) Field of Classification Search
USPC .............. 428/690, 917; 313/504, 505, 506; 257/40, E51.05, E51.026, E51.032; 548/304.4, 440, 418, 444
See application file for complete search history.

(56) References Cited

U.S. PATENT DOCUMENTS

| 5,645,948 A | 7/1997 | Shi et al. |
| 2005/0004114 A1 | 1/2005 | Whitehouse et al. |

(Continued)

FOREIGN PATENT DOCUMENTS

| JP | 10 092578 | 4/1998 |
| JP | 2002 38141 | 2/2002 |

(Continued)

OTHER PUBLICATIONS

Katritzky, R. Alan et al., "A 1, 4-Photochemical Aryl Shift", Tetrahedron Letter, vol. 23, No. 12, pp. 1241-1242, (1982).
(Continued)

*Primary Examiner* — Gregory Clark
(74) *Attorney, Agent, or Firm* — Oblon, Spivak, McClelland, Maier & Neustadt, L.L.P.

(57) ABSTRACT

A novel nitrogen-containing heterocyclic derivative having a specific structure. An organic electroluminescence device comprises an organic thin-film layer which is disposed between a cathode and an anode and comprises one or more layers having a light emitting layer. At least one layer of the organic thin-film layer comprises the nitrogen-containing heterocyclic derivative. The organic electroluminescence device exhibits a high luminance and a high luminous efficiency even at a low driving voltage.

16 Claims, 1 Drawing Sheet

(51) Int. Cl.
*C07D 235/08* (2006.01)
*C07D 235/18* (2006.01)
*C07D 401/04* (2006.01)
*C07D 401/10* (2006.01)
*C07D 403/10* (2006.01)
*C07D 471/04* (2006.01)
*H01L 51/00* (2006.01)
*H05B 33/14* (2006.01)
*H01L 51/50* (2006.01)

(52) U.S. Cl.
CPC .......... *C07D 401/04* (2013.01); *C07D 401/10* (2013.01); *C07D 403/10* (2013.01); *C07D 471/04* (2013.01); *H01L 51/0072* (2013.01); *H05B 33/14* (2013.01); *C09K 2211/1007* (2013.01); *C09K 2211/1011* (2013.01); *C09K 2211/1044* (2013.01); *H01L 51/0052* (2013.01); *H01L 51/0054* (2013.01); *H01L 51/0055* (2013.01); *H01L 51/0058* (2013.01); *H01L 51/006* (2013.01); *H01L 51/5012* (2013.01); *H01L 51/5048* (2013.01); *H01L 51/5092* (2013.01); *Y10S 428/917* (2013.01)
USPC .......... 428/690; 428/917; 313/504; 313/505; 313/506; 257/40; 257/E51.05; 257/E51.026; 257/E51.032; 548/304.4; 548/418; 548/440; 548/444

(56) References Cited

U.S. PATENT DOCUMENTS

| | | |
|---|---|---|
| 2005/0187390 A1 | 8/2005 | Schmitz et al. |
| 2006/0147747 A1 | 7/2006 | Yamamoto et al. |
| 2007/0018155 A1 | 1/2007 | Bae et al. |
| 2007/0138950 A1 | 6/2007 | Yamamoto et al. |
| 2007/0200490 A1 | 8/2007 | Kawamura et al. |
| 2007/0267970 A1* | 11/2007 | Yamamoto et al. .......... 313/506 |
| 2007/0280928 A1 | 12/2007 | Buck et al. |
| 2008/0018237 A1 | 1/2008 | Yamamoto et al. |
| 2009/0140637 A1 | 6/2009 | Hosokawa et al. |
| 2009/0278115 A1 | 11/2009 | Hosokawa et al. |

FOREIGN PATENT DOCUMENTS

| | | | |
|---|---|---|---|
| JP | 2005-113072 | * 4/2005 | ............ C09K 11/06 |
| WO | 2004 080975 | 9/2004 | |
| WO | 2004 099192 | 11/2004 | |
| WO | 2005 012288 | 2/2005 | |
| WO | 2005 097756 | 10/2005 | |
| WO | 2007 007463 | 1/2007 | |
| WO | 2007 011170 | 1/2007 | |
| WO | 2007 106503 | 9/2007 | |
| WO | 2008 067644 | 6/2008 | |
| WO | 2008 073451 | 6/2008 | |
| WO | 2008 105515 | 9/2008 | |

OTHER PUBLICATIONS

International Search Report issued Feb. 3, 2009 in PCT/JP08/73457 filed Dec. 24, 2008.

* cited by examiner

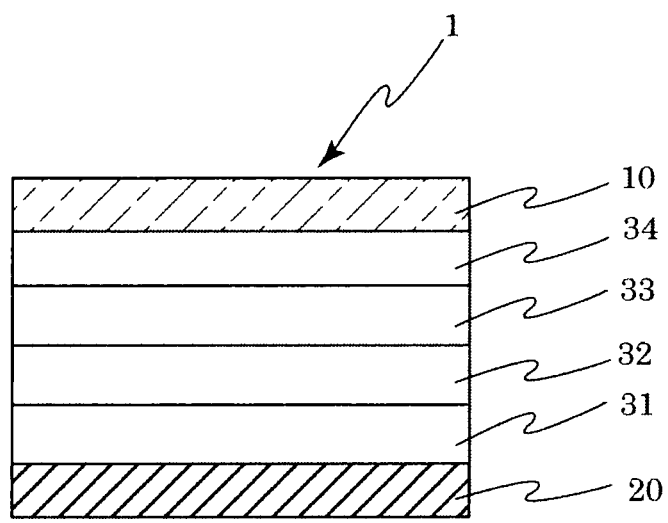

NITROGEN-CONTAINING HETEROCYCLIC DERIVATIVE AND ORGANIC ELECTROLUMINESCENT DEVICE USING THE SAME

TECHNICAL FIELD

The present invention relates to a novel nitrogen-containing heterocyclic derivative and a material for an organic electroluminescence device (organic EL device) comprising the derivative and an organic EL device using the derivative, and particularly relates to an organic EL device which exhibits a high luminous efficiency even at a low driving voltage because at least one layer of the organic compound layer contains the nitrogen-containing heterocyclic derivative useful as a component for constituting an organic EL device.

BACKGROUND ART

Organic EL devices utilizing organic substances are much expected to be useful as inexpensive, large-sized full color display devices of solid state emission type and many developments have been made thereon. An organic EL device is generally constructed from a light emitting layer and a pair of opposite electrodes sandwiching the light emitting layer. When an electric field is applied between the electrodes, electrons are injected from a cathode and holes are injected from an anode. The injected electrons recombine with the injected holes in the light emitting layer to form excited states. When the excited states return to the ground state, the energy is released as light.

Known organic EL devices have a higher driving voltage, a lower luminance, and a lower emission efficiency than those of inorganic light emitting diodes. In addition, the properties thereof are drastically deteriorated to make the practical use difficult. Although the organic EL device has been gradually improved, a high luminance and a high luminous efficiency at lower voltage has been required.

To solve the above problems, a device containing a compound having a benzimidazole structure as the light emitting material is disclosed in Patent Document 1. It is described that this device shows a luminance of 200 cd/m² at a voltage of 9 V. A compound having a benzimidazole ring and an anthracene residue is described in Patent Documents 2 and 3. However, a luminance and a luminous efficiency still higher than those of organic EL devices employing these compounds are required.

Patent Document 1: JP 10-092578A (U.S. Pat. No. 5,645,948)
Patent Document 2: JP 2002-38141A
Patent Document 3: WO 2004/080975 (US 2006/147747)

DISCLOSURE OF THE INVENTION

The present invention has been made to solve the above problems, and an object of the invention is to provide a novel nitrogen-containing heterocyclic derivative useful as a material for constituting an organic EL device and another object is to realize an organic EL device which exhibits a high luminance and a high luminous efficiency even at a low voltage by using the nitrogen-containing heterocyclic derivative in at least one layer of organic compound layers.

As a result of extensive researches in view of achieving the above objects, the inventors have found that a high efficiency and a low driving voltage of organic EL device is achieved by using a novel nitrogen-containing heterocyclic derivative having a specific structure in at least one layer of the organic compound layers of an organic EL device and made the present invention.

The present invention provides a nitrogen-containing heterocyclic derivative (benzimidazole compound) represented by formula (1):

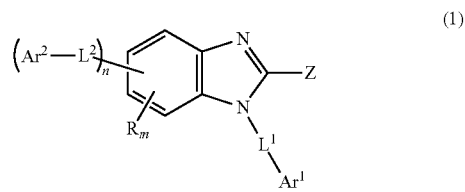

wherein
R is hydrogen atom, a substituted or unsubstituted alkyl group having 1 to 50 carbon atoms, a substituted or unsubstituted cycloalkyl group having 3 to 50 ring-forming carbon atoms, a substituted or unsubstituted haloalkyl group having 1 to 50 carbon atoms, a substituted or unsubstituted aryl group having 6 to 20 ring-forming carbon atoms, a substituted or unsubstituted heteroaryl group having 5 to 20 ring-forming atoms, halogen atom, cyano group, or nitro group;

m is an integer of 0 to 4, and when m is an integer of 2 to 4 R groups may be the same or different and adjacent pair of R groups may be bonded to each other to form a substituted or unsubstituted, saturated or unsaturated linking group which completes a ring structure;

$L^1$ and $L^2$ are each independently a single bond, a substituted or unsubstituted arylene group having 6 to 20 ring-forming carbon atoms, or a substituted or unsubstituted heteroarylene group having 5 to 20 ring-forming atoms, with the proviso that a substituted or unsubstituted anthracenylene group and a substituted or unsubstituted fluorenylene group are excluded;

$Ar^1$ is hydrogen atom, a substituted or unsubstituted alkyl group having 1 to 50 carbon atoms, a substituted or unsubstituted cycloalkyl group having 3 to 50 ring-forming carbon atoms, a substituted or unsubstituted haloalkyl group having 1 to 50 carbon atoms, a substituted or unsubstituted aryl group having 6 to 20 ring-forming carbon atoms, or a substituted or unsubstituted heteroaryl group having 5 to 20 ring-forming atoms, with the proviso that anthracenyl group, carbazolyl group, azacarbazolyl group, benzimidazolyl group, dibenzofuryl group, and dibenzothienyl group are excluded;

$Ar^2$ is hydrogen atom, a substituted or unsubstituted aryl group having 6 to 20 ring-forming carbon atoms, or a substituted or unsubstituted heteroaryl group having 5 to 20 ring-forming atoms, with the proviso that anthracenyl group is excluded;

n is an integer of 0 to 4, and when n is 0 $L^1$ is not a single bond and $Ar^1$ is not hydrogen atom, and when n is an integer of 2 to 4 $Ar^2$ groups and $L^2$ groups may be the same or different, respectively;

Z is $-R^a$ or $-L^3-Ar^3$;

$R^a$ is hydrogen atom; a substituted or unsubstituted alkyl group having 1 to 50 carbon atoms; a substituted or unsubstituted cycloalkyl group having 3 to 50 ring-forming carbon atoms; a non-condensed aryl group having 6 to 20 ring-forming carbon atoms which may be substituted by an alkyl group; a substituted or unsubstituted, condensed polycyclic aryl group having 6 to 20 ring-forming carbon atoms; a non-condensed heteroaryl group having 5 to 20 ring-forming atoms which may be substituted by an alkyl group, a non-condensed aryl group or a non-condensed heteroaryl group; or a substituted or unsubstituted condensed polycyclic heteroaryl group having 5 to 20 ring-forming atoms;

$L^3$ is a substituted or unsubstituted arylene group having 6 to 20 ring-forming carbon atoms or a substituted or unsubstituted heteroarylene group having 5 to 20 ring-forming atoms, with the proviso that a substituted or unsubstituted anthracenylene group and a substituted or unsubstituted fluorenylene group are excluded;

$Ar^3$ is a substituted or unsubstituted aryl group having 6 to 20 ring-forming carbon atoms or a substituted or unsubstituted heteroaryl group having 5 to 20 ring-forming atoms, with the proviso atha anthracenyl group, carbazolyl group, azacarbazolyl group, benzimidazolyl group, dibenzofuryl group, and dibenzothienyl group are excluded;

n is not zero when Z is $-R^a$ and $Ar^1$ is hydrogen atom, a substituted or unsubstituted alkyl group having 1 to 50 carbon atoms, a substituted or unsubstituted cycloalkyl group having 3 to 50 ring-forming carbon atoms, or a substituted or unsubstituted haloalkyl group having 1 to 50 carbon atoms; and when Z is $-L^3-Ar^3$, $L^1$ and $L^2$ cannot be a single bond at the same time, and $Ar^1$ and $Ar^2$ cannot be hydrogen atom at the same time.

The present invention further provides an organic EL device comprising an organic thin-film layer which is disposed between a cathode and an anode and comprises one or more layers having a light emitting layer, wherein at least one layer of the organic thin-film layer comprises the nitrogen-containing heterocyclic derivative of formula (1) mentioned above.

The nitrogen-containing heterocyclic derivative of the invention and the organic EL device employing such a derivative exhibit a high luminous efficiency and a good electron transporting property even at a low driving voltage.

BRIEF DESCRIPTION OF DRAWINGS

FIG. 1 is a schematic cross-sectional view showing a preferred layered structure of the organic electroluminescence device of the invention.

BEST MODE FOR CARRYING OUT THE INVENTION

The nitrogen-containing heterocyclic derivative of the invention is represented by formula (1).

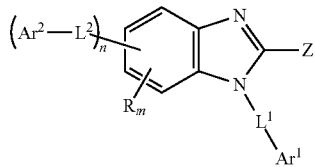

In formula (1), Z is $-R^a$ or $-L^3-Ar^3$.

$R^a$ is hydrogen atom; a substituted or unsubstituted alkyl group having 1 to 50 carbon atoms; a substituted or unsubstituted cycloalkyl group having 3 to 50 ring-forming carbon atoms; a non-condensed aryl group having 6 to 20 ring-forming carbon atoms which may be substituted by an alkyl group; a substituted or unsubstituted, condensed polycyclic aryl group having 5 to 20 ring-forming carbon atoms, a non-condensed heteroaryl group having 5 to 20 ring-forming atoms which may be substituted by an alkyl group, a non-condensed aryl group or a non-condensed heteroaryl group; or a substituted or unsubstituted, condensed polycyclic heteroaryl group having 5 to 20 ring-forming atoms.

Examples of the substituted or unsubstituted alkyl group for $R^a$ include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, and 1,2,3-trinitropropyl group.

Examples of the substituted or unsubstituted cycloalkyl group for $R^a$ include cyclopropyl group, cyclobutyl group, cyclopentyl group, cyclohexyl group, 4-methylcyclohexyl group, 1-adamantyl group, 2-adamantyl group, 1-norbornyl group, and 2-norbornyl group.

Examples of the non-condensed aryl group optionally substituted by an alkyl group for $R^a$ include phenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 4'-methylbiphenylyl group, and 4"-t-butyl-p-terphenyl-4-yl group. Examples of the alkyl group as the substituent for the non-condensed aryl group include the alkyl groups having 1 to 50 carbon atoms mentioned above.

Examples of the substituted or unsubstituted condensed polycyclic aryl group for $R^a$ include 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 3-methyl-2-naphthyl group, 4-methyl-1-naphthyl group, 4-methyl-1-anthryl group, fluoranthenyl group, and fluorenyl group.

Examples of the non-condensed heteroaryl group which may be substituted by an alkyl group, a non-condensed aryl group or a non-condensed heteroaryl group for $R^a$ include 1-pyrrolyl group, 2-pyrrolyl group, 3-pyrrolyl group, pyrazinyl group, 2-pyridinyl group, 3-pyridinyl group, 4-pyridinyl group, 2-furyl group, 3-furyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2,2'-bipyridinyl group, and 2,2':6',2''-bipyridinyl group. The alkyl group, non-condensed aryl group and non-condensed heteroaryl group as the substituents for the non-condensed heteroaryl group are respectively selected from the alkyl groups having 1 to 50 carbon atoms, the non-condensed aryl groups having 6 to 20 ring-forming carbon atoms and the non-condensed heteroaryl groups having 5 to 20 ring-forming atoms each mentioned above.

Examples of the substituted or unsubstituted, condensed polycyclic heteroaryl group for $R^a$ include 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

R is hydrogen atom, a substituted or unsubstituted alkyl group having 1 to 50 carbon atoms, a substituted or unsubstituted cycloalkyl group having 3 to 50 ring-forming carbon atoms, a substituted or unsubstituted haloalkyl group having 1 to 50 carbon atoms, a substituted or unsubstituted aryl group having 6 to 20 ring-forming carbon atoms, a substituted or unsubstituted heteroaryl group having 5 to 20 ring-forming atoms, halogen atom, cyano group, or nitro group.

The substituted or unsubstituted alkyl group and the substituted or unsubstituted cycloalkyl group having 3 to 50 ring-forming carbon atoms for R are respectively selected from the (substituted) alkyl groups and the (substituted) cycloalkyl groups which are mentioned with respect to $R^a$.

The substituted or unsubstituted haloalkyl group for R is selected from the groups which are derived from the alkyl group having 1 to 50 carbon atoms mentioned above by replacing its hydrogen atom with a halogen atom selected from fluorine atom, chlorine atom, bromine atom, and iodine atom. Examples thereof include trifluoromethyl group, 2,2,2-trifluoroethyl group, pentafluoroethyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, and 1,2,3-triiodopropyl group.

Examples of the substituted or unsubstituted aryl group for R include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4''-t-butyl-p-terphenyl-4-yl group, fluoranthenyl group, and fluorenyl group.

Examples of the substituted or unsubstituted heteroaryl group for R include 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

Examples of the halogen atom for R include fluorine atom, chlorine atom, bromine atom, and iodine atom.

Subscript m is an integer of 0 to 4. When m is an integer of 2 to 4, R groups may be the same or different, and the adjacent pair of R groups may be bonded to each other to form a substituted or unsubstituted, saturated or unsaturated linking group which completes a ring structure.

$L^1$ and $L^2$ are each independently a single bond, a substituted or unsubstituted arylene group having 6 to 20 ring-forming carbon atoms, or a substituted or unsubstituted heteroarylene group having 5 to 20 ring-forming atoms, with the proviso that a substituted or unsubstituted anthracenylene group and a substituted or unsubstituted fluorenylene group are excluded.

$L^3$ is a substituted or unsubstituted arylene group having 6 to 20 ring-forming carbon atoms or a substituted or unsubstituted heteroarylene group having 5 to 20 ring-forming atoms, with the proviso that a substituted or unsubstituted anthracenylene group and a substituted or unsubstituted fluorenylene group are excluded.

The substituted or unsubstituted arylene group for $L^1$ to $L^3$ is selected from the divalent groups which are derived from the substituted or unsubstituted aryl group mentioned with respect to R by removing one hydrogen atom. Similarly, the substituted or unsubstituted heteroarylene group is selected from the divalent groups which are derived from the substituted or unsubstituted heteroaryl group mentioned with respect to R by removing one hydrogen atom. Particularly preferred groups for $L^1$ to $L^3$ are p-phenylene group, m-phenylene group, pyridine-2,6-diyl group, and biphenyl-4,4'-diyl group.

$Ar^1$ is hydrogen atom, a substituted or unsubstituted alkyl group having 1 to 50 carbon atoms, a substituted or unsubstituted cycloalkyl group having 3 to 50 ring-forming carbon atoms, a substituted or unsubstituted haloalkyl group having 1 to 50 carbon atoms, a substituted or unsubstituted aryl group having 6 to 20 ring-forming carbon atoms, or a substituted or unsubstituted heteroaryl group having 5 to 20 ring-forming atoms, with the proviso that anthracenyl group, carbazolyl group, azacarbazolyl group, benzimidazolyl group, dibenzofuryl group, and dibenzothienyl group are excluded.

The substituted or unsubstituted alkyl group and the substituted or unsubstituted cycloalkyl group for $Ar^1$ is selected from the (substituted) alkyl group and the (substituted) cycloalkyl group mentioned with respect to $R^a$. The substituted or unsubstituted haloalkyl group, the substituted or unsubstituted aryl group, and the substituted or unsubstituted heteroaryl group for $Ar^1$ are respectively selected from the (substituted) haloalkyl group, the (substituted) aryl group (exclusive of anthracenyl group), and the (substituted) heteroaryl group (exclusive of carbazolyl group, azacarbazolyl group, benzimidazolyl group, dibenzofuryl group, and dibenzothienyl group) each mentioned above with respect to R.

$Ar^2$ is hydrogen atom, a substituted or unsubstituted aryl group having 6 to 20 ring-forming carbon atoms, or a substituted or unsubstituted heteroaryl group having 5 to 20 ring-forming atoms, with the proviso that anthracenyl group is excluded.

The substituted or unsubstituted aryl group and the substituted or unsubstituted heteroaryl group for $Ar^2$ are selected from the (substituted) aryl group (exclusive of anthracenyl group) and the (substituted) heteroaryl group which are mentioned above with respect to R.

$Ar^3$ is a substituted or unsubstituted aryl group having 6 to 20 ring-forming carbon atoms or a substituted or unsubstituted heteroaryl group having 5 to 20 ring-forming atoms, with the proviso that anthracenyl group, carbazolyl group, azacarbazolyl group, benzimidazolyl group, dibenzofuryl group, and dibenzothienyl group are excluded.

The substituted or unsubstituted aryl group and the substituted or unsubstituted heteroaryl group for $Ar^3$ are selected from the (substituted) aryl group (exclusive of anthracenyl group) and the (substituted) heteroaryl group (exclusive of carbazolyl group, azacarbazolyl group, benzimidazolyl group, dibenzofuryl group, and dibenzothienyl group) which are mentioned above with respect to R.

It is preferred that at least one of $Ar^1$ to $Ar^3$ is a monovalent group which is formed from any of the following condensed ring compounds by removing any one of hydrogen atom.

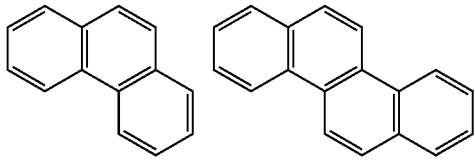
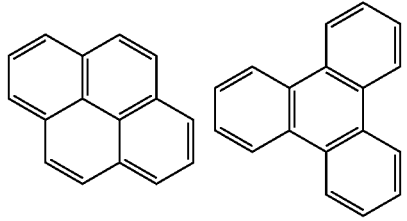
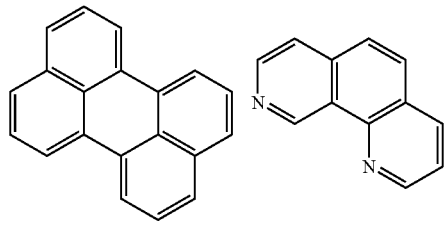
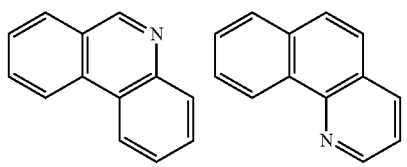
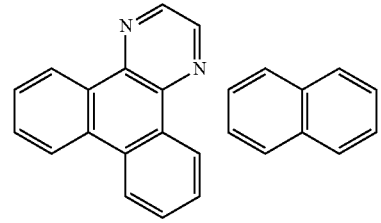

The position of the free bond of the monovalent condensed ring group is not particularly limited, with the following condensed ring groups being preferred.

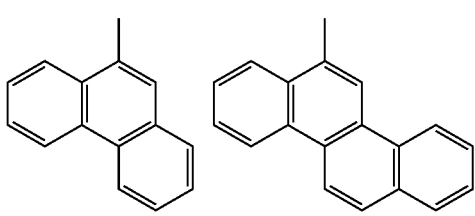
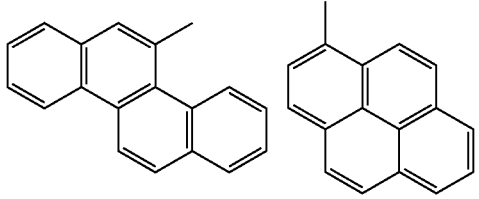
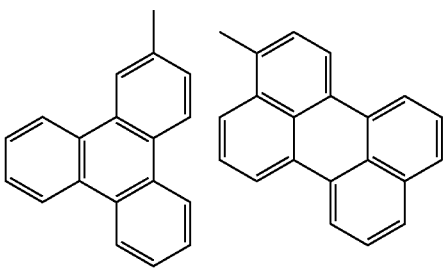
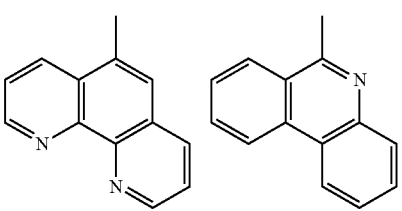
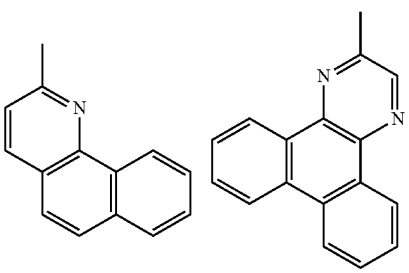
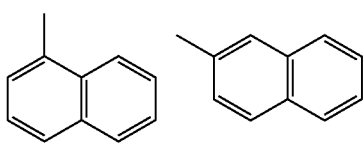

Subscript n is an integer of 0 to 4. When n is an integer of 2 to 4, $Ar^2$ groups and $L^2$ groups may be the same or different, respectively. When n is zero, $L^1$ is not a single bond and $Ar^1$ is not hydrogen atom.

When Z is $-R^a$ and $Ar^1$ is hydrogen atom, a substituted or unsubstituted alkyl group having 1 to 50 carbon atoms, a substituted or unsubstituted cycloalkyl group having 3 to 50 ring-forming carbon atoms, or a substituted or unsubstituted haloalkyl group having 1 to 50 carbon atoms, n is not zero, i.e. n is an integer of 1 to 4.

When Z is $-L^3-Ar^3$, $L^1$ and $L^2$ cannot be a single bond at the same time, and $Ar^1$ and $Ar^2$ cannot be hydrogen atom at the same time.

The nitrogen-containing heterocyclic derivative of formula (1) is preferably represented by formula (1a) or (1b):

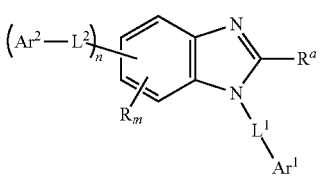

(1a)

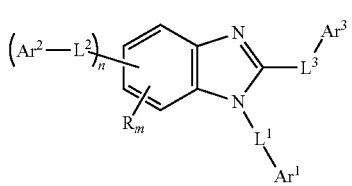
(1b)

wherein $R^a$, R, m, $L^1$, $L^2$, $L^3$, $Ar^1$, $Ar^2$, $Ar^3$, and n are as defined above.

The nitrogen-containing heterocyclic derivative of formula (1a) is preferably represented by any of formulae (2a) to (5a).

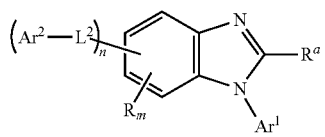
(2a)

In formula (2a), $R^a$, R, m, $L^2$, $Ar^1$, $Ar^2$, and n are as defined above.

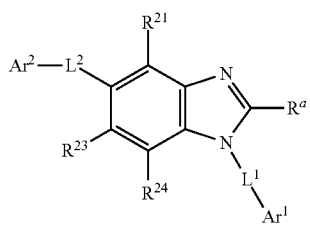
(3a)

In formula (3a), $R^a$, $L^1$, $L^2$, $Ar^1$, and $Ar^2$ are as defined above, and $R^{21}$, $R^{23}$ and $R^{24}$ are the same as R of formula (1).

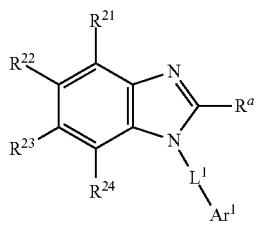
(4a)

In formula (4a), $R^a$, $L^1$, and $Ar^1$ are as defined above, and $R^{21}$ to $R^{24}$ are the same as R of formula (1).

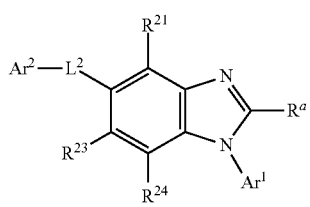
(5a)

In formula (5a), $R^a$, $L^2$, $Ar^1$, and $Ar^2$ are as defined above, and $R^{21}$, $R^{23}$ and $R^{24}$ are the same as R of formula (1).

The nitrogen-containing heterocyclic derivative of formula (1b) is preferably represented by any of formulae (2b) to (5b).

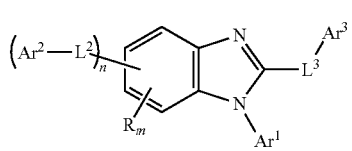
(2b)

In formula (2b), R, m, $L^2$, $L^3$, $Ar^1$, $Ar^2$, $Ar^3$, and n are as defined above.

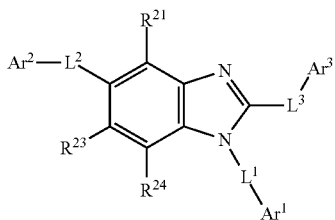
(3b)

In formula (3b), $L^1$ to $L^3$ and $Ar^1$ to $Ar^3$ are as defined above, and $R^{21}$, $R^{23}$ and $R^{24}$ are the same as R of formula (1).

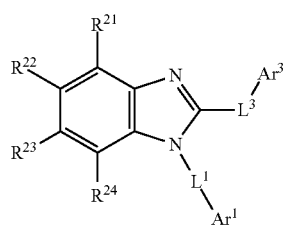
(4b)

In formula (4b), $L^1$, $L^3$, $Ar^1$ and $Ar^3$ are as defined above, and $R^{21}$ and $R^{24}$ are the same as R of formula (1).

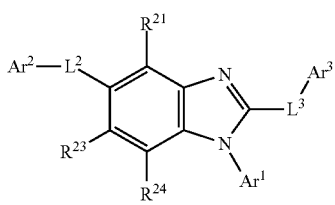
(5b)

In formula (5b), $L^2$, $L^3$, and $Ar^1$ to $Ar^3$ are as defined above, and $R^{21}$, $R^{23}$ and $R^{24}$ are the same as R of formula (1).

Examples of the optional substituent group for "substituted or unsubstituted . . . group" mentioned above include an alkyl group having 1 to 20 carbon atoms, a cycloalkyl group having 3 to 20 carbon atoms, an aryl group having 6 to 20 ring-forming carbon atoms, a heteroaryl group having 3 to 20 ring-forming carbon atoms, an alkoxy group having 1 to 20 carbon atoms, a cycloalkoxy group having 3 to 20 carbon atoms, an aryloxy group having 6 to 30 ring-forming carbon atoms, an aralkyl group having 7 to 31 carbon atoms, a halogen atom, nitro group, cyano group, and hydroxyl group.

The compound of formula (1) (BI-AR) is synthesized by the coupling reaction between a halide of a corresponding benzimidazole (BI-X, inclusive of a halide of an aryl-substituted benzimidazole) and a boronic acid or boronic ester derivative of a corresponding condensed ring compound (AR-B(OR')$_2$), or by the reaction between a boronic acid or boronic ester derivative of a benzimidazole (BI-B(OR')$_2$) and a halide of a corresponding condensed ring compound (AR- X, inclusive of a halide of an aryl-substituted condensed ring compound) using a common Suzuki coupling reaction or a method described in Tetrahedron Lett., 38, 3447 (1997), Tetrahedron Lett., 38, 3841 (1997), and Tetrahedron Lett., 38, 1197 (1997). The reaction conditions, etc. are selected and determined easily by a person skilled in the art.

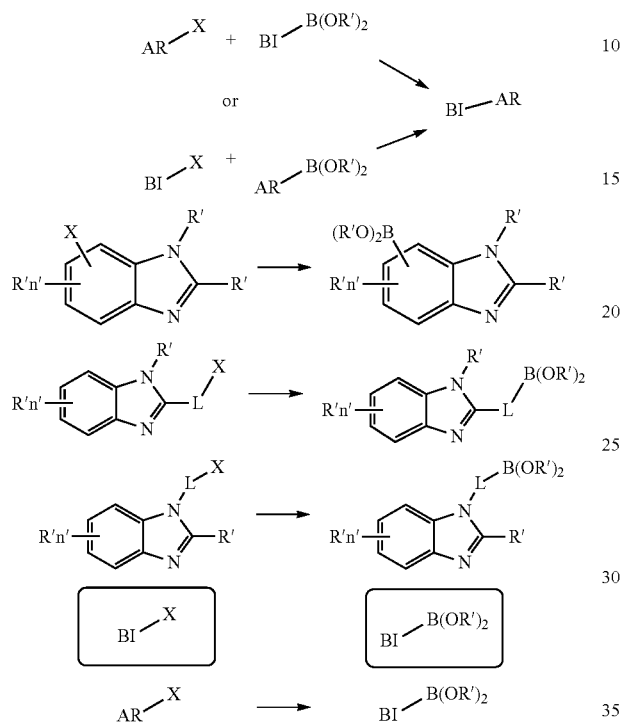

In the above formulae, X is a halogen atom, and R', n' and L are groups and integer which are selected so as to meet the definitions of Z, R, m, $L^1$, $L^2$, $Ar^1$, $Ar^2$, and n of formula (1).

The nitrogen-containing heterocyclic derivative of formula (1) is preferably used as a material for organic EL devices, particularly as a light emitting material, an electron injecting material or a electron transporting material.

Examples of the nitrogen-containing heterocyclic derivative represented by formula (1a) are shown below, although not limited to the following exemplary compounds.

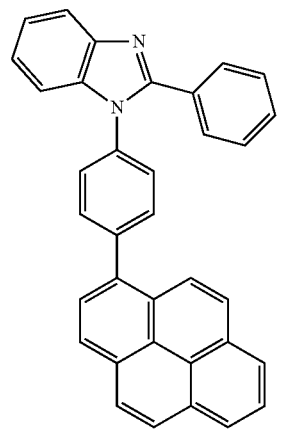

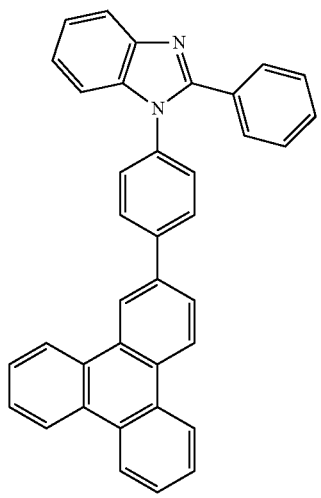

-continued

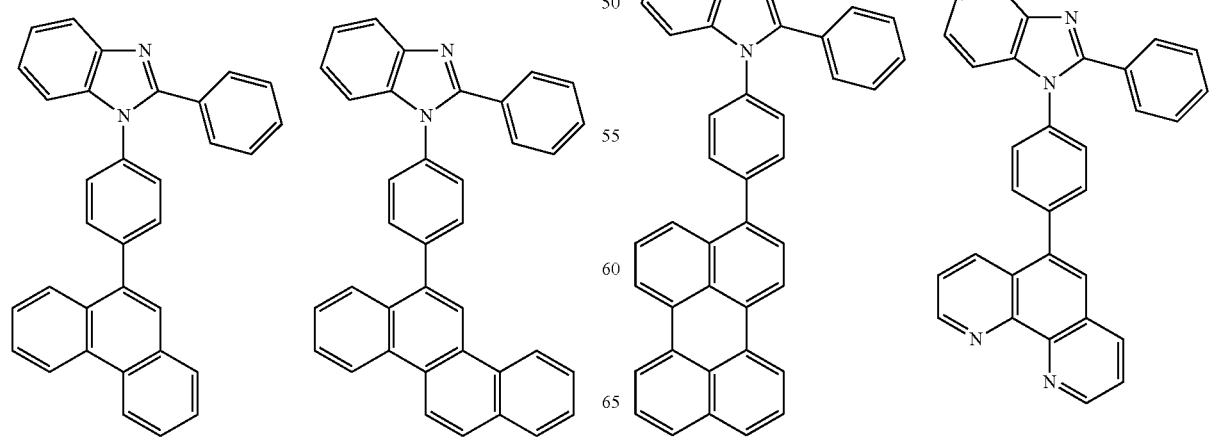

15
-continued
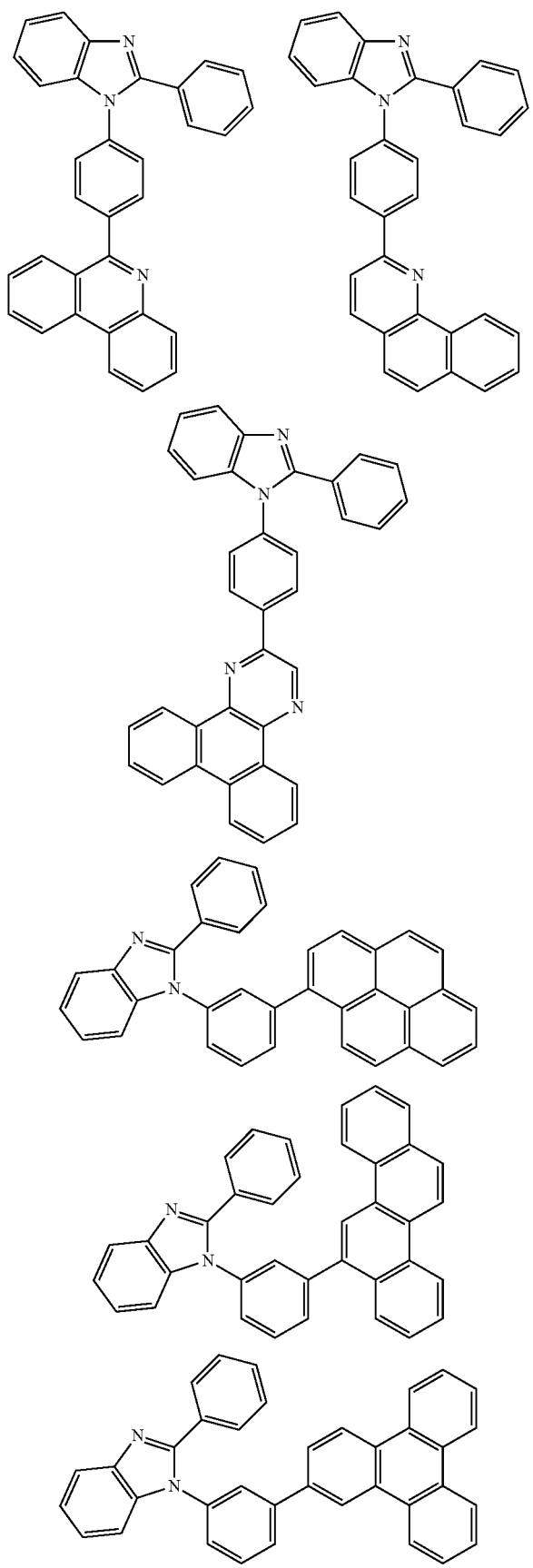
16
-continued
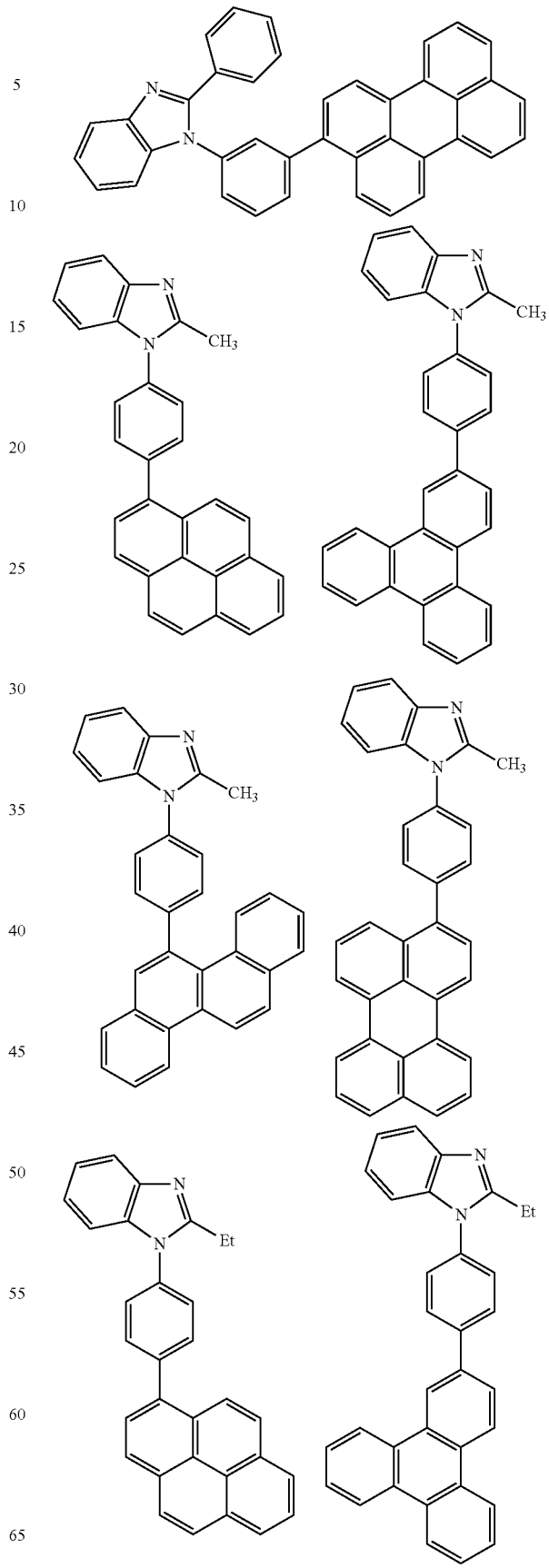

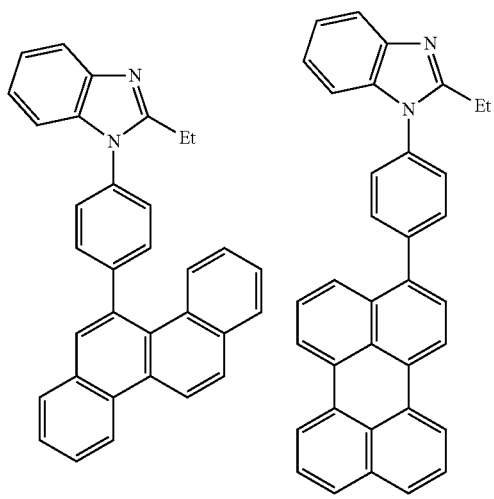
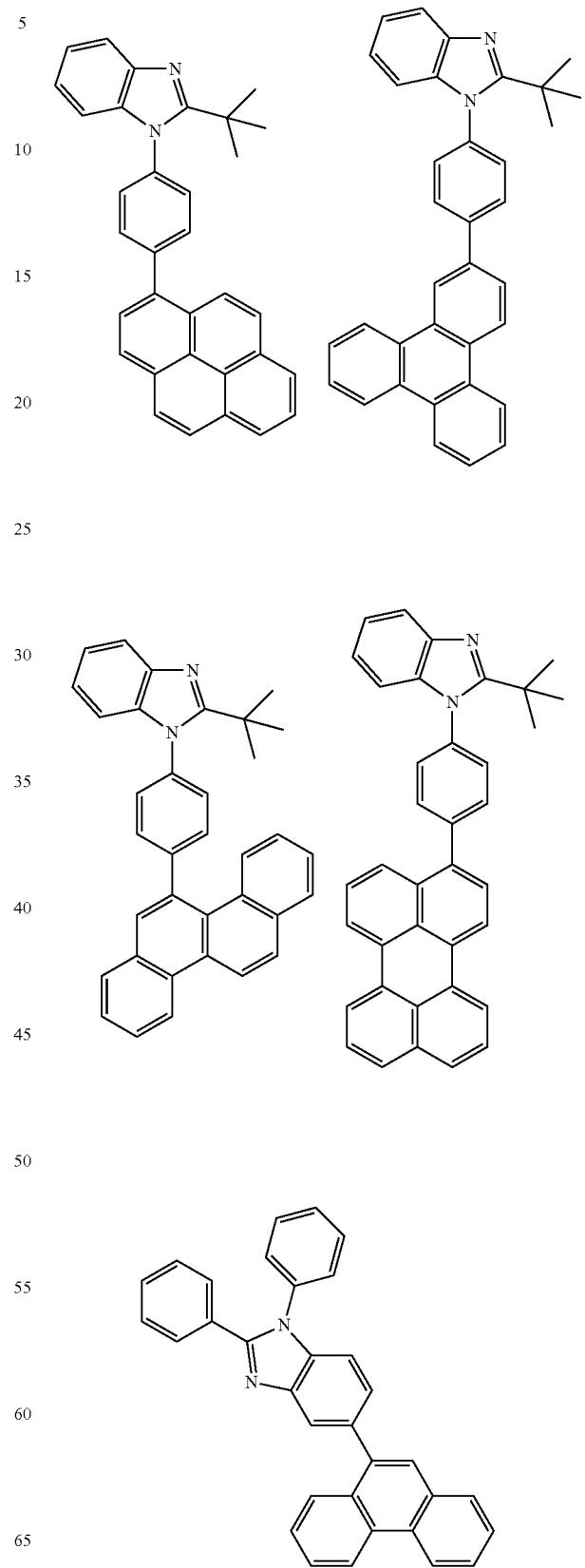

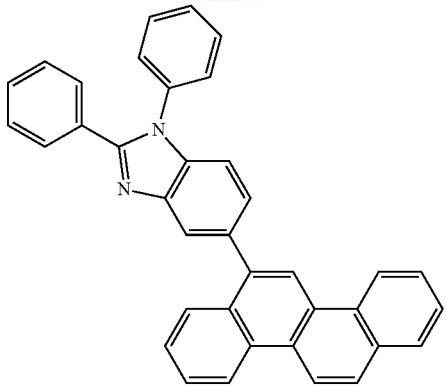
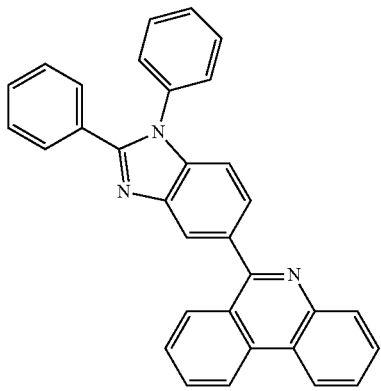
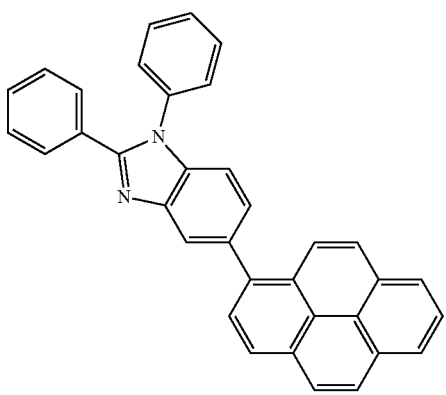
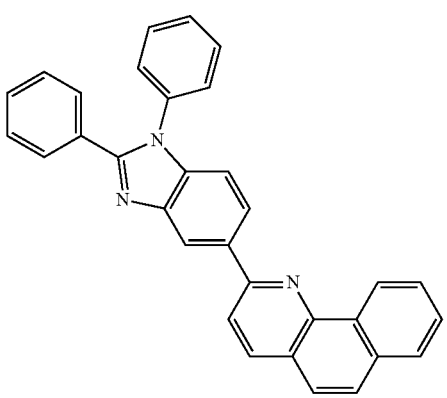
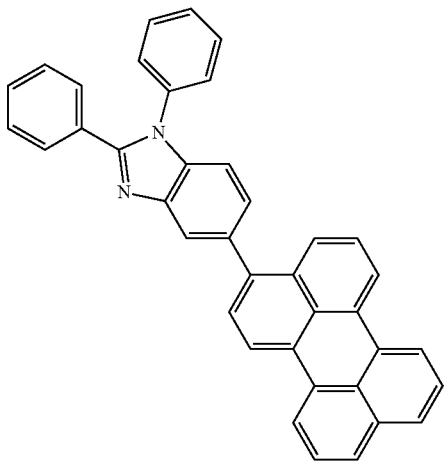
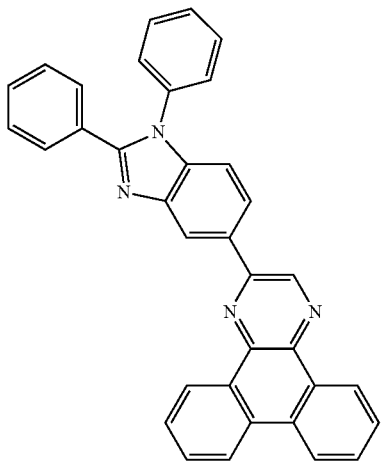
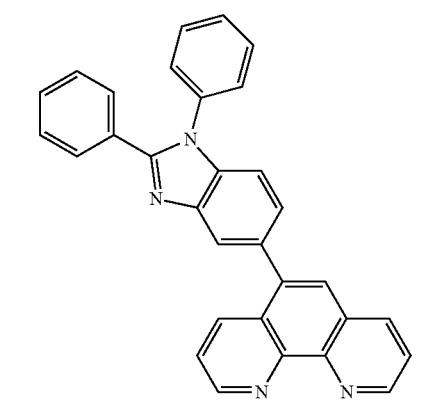
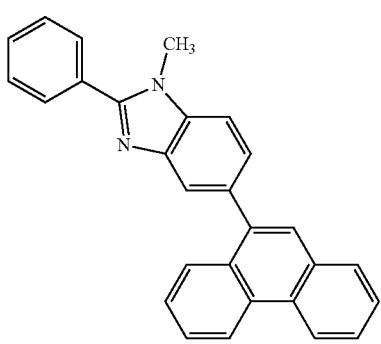

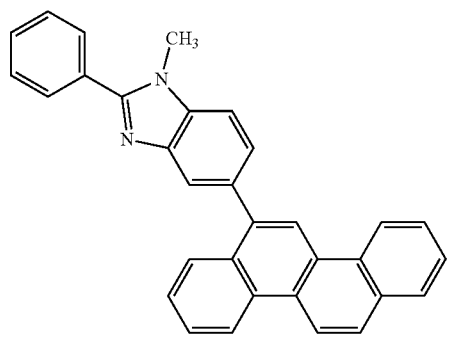
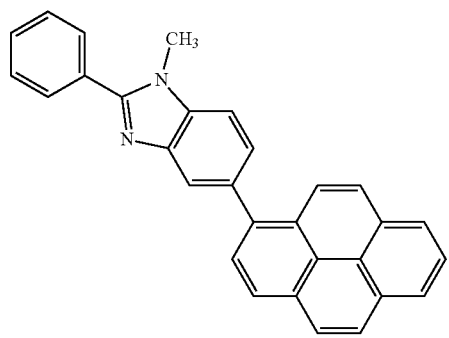
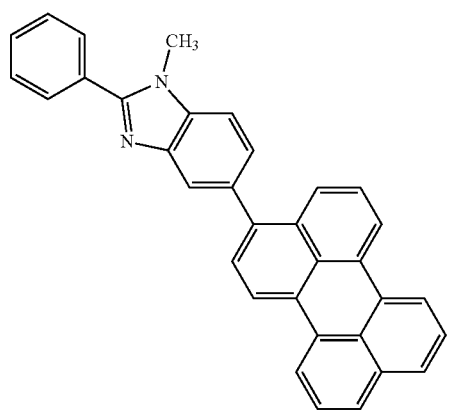
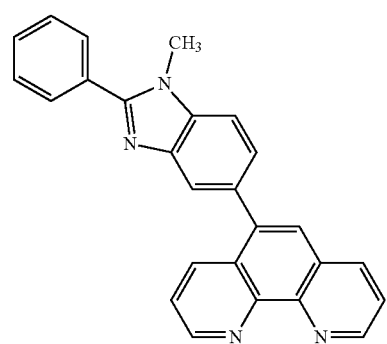
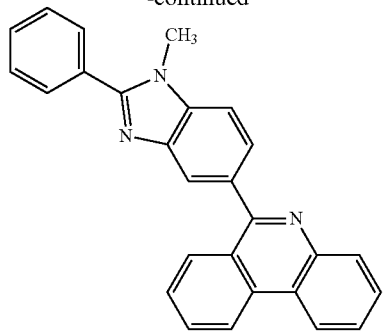
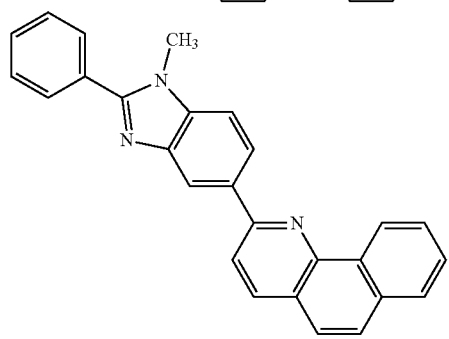
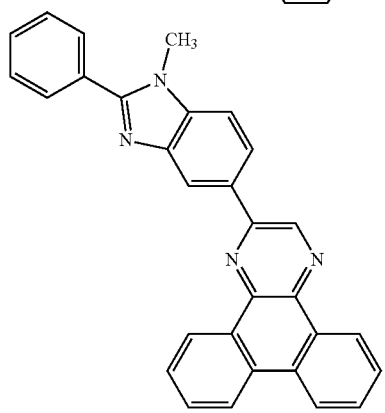
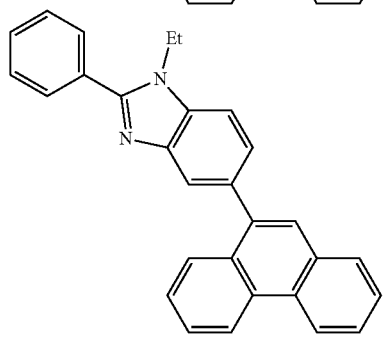
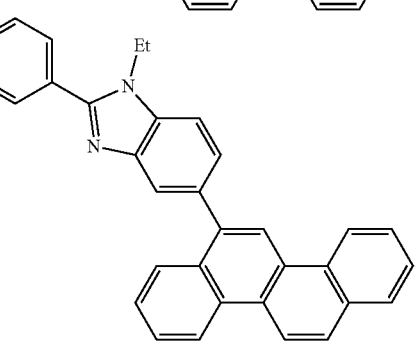

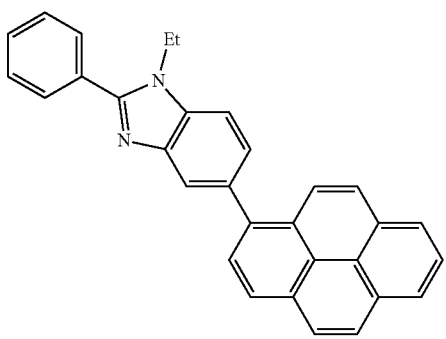
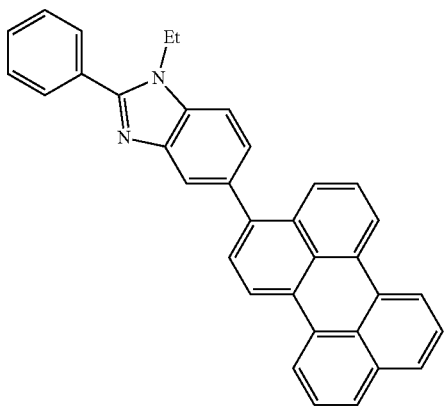
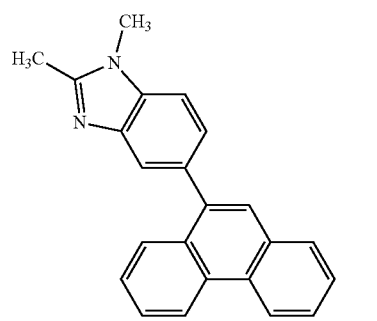
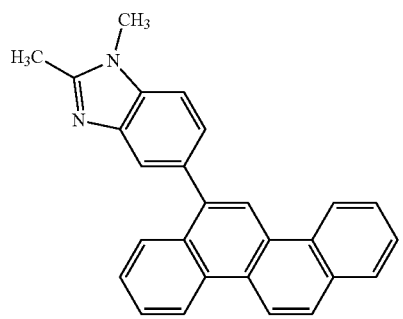
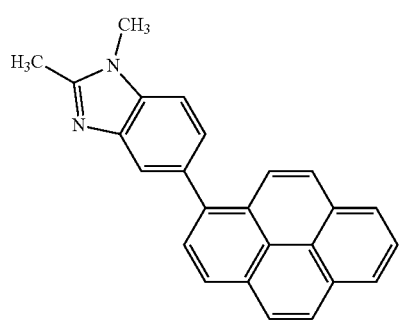
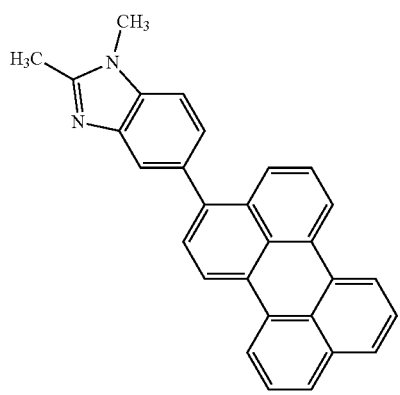
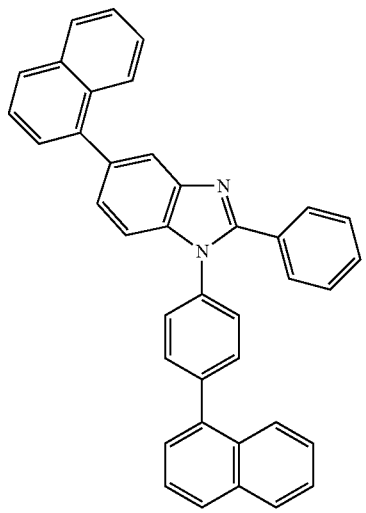
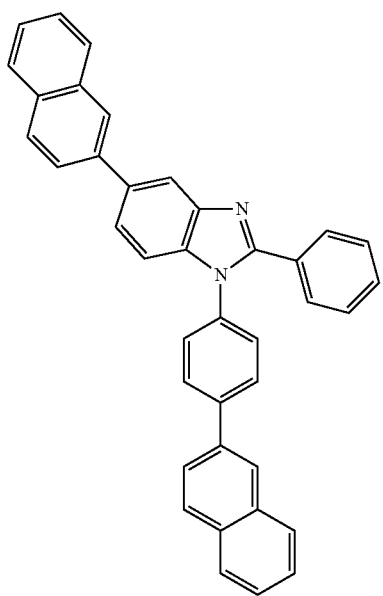

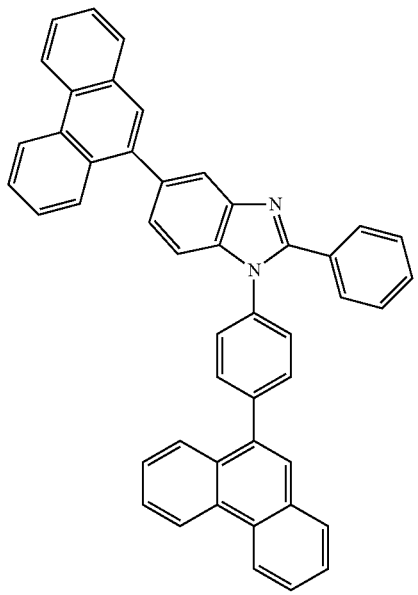
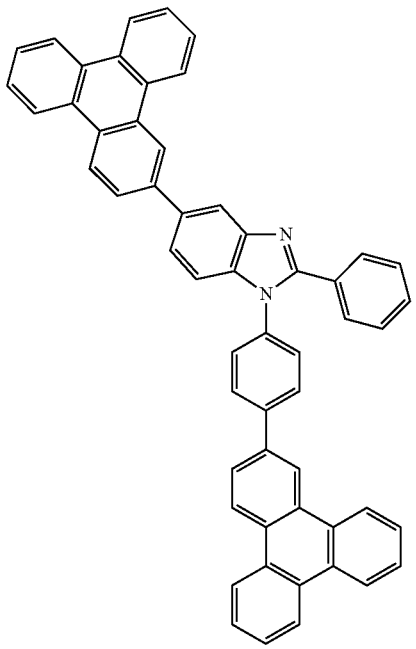
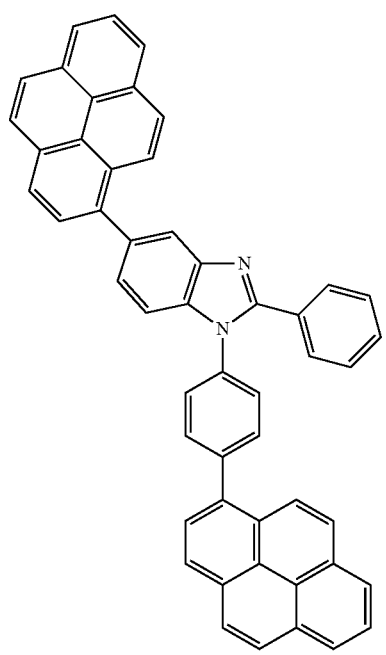
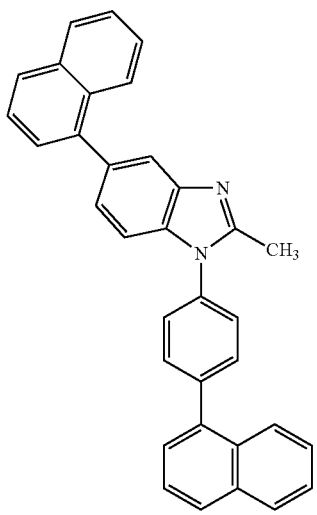

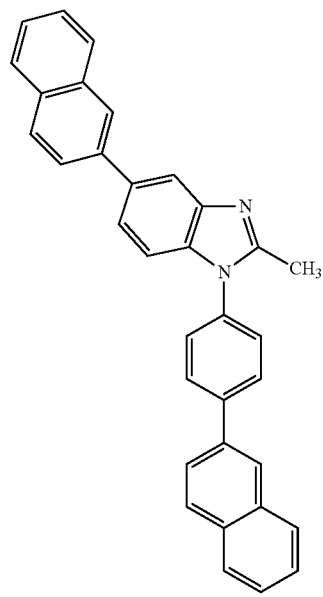
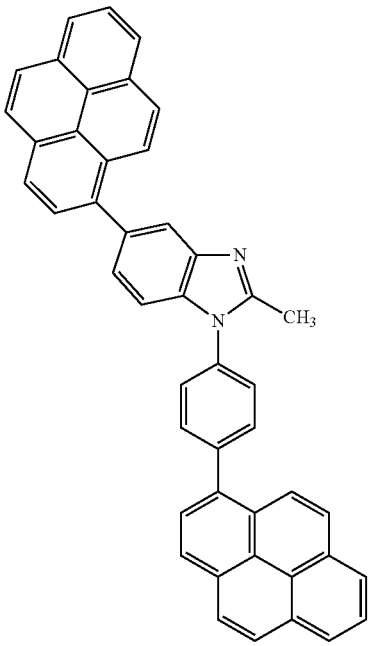
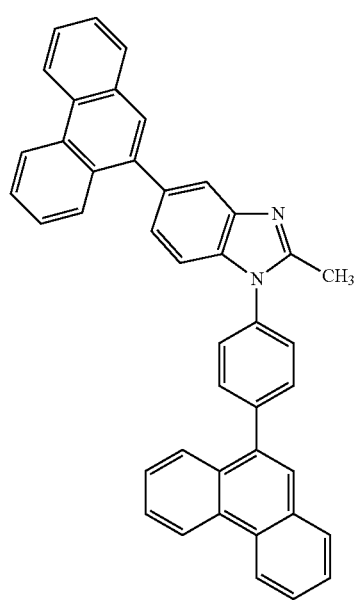
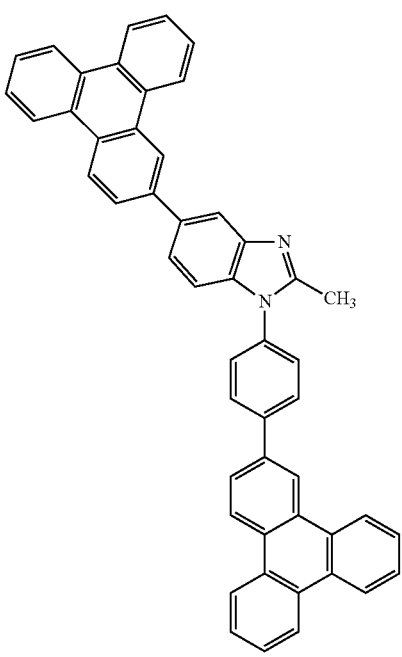

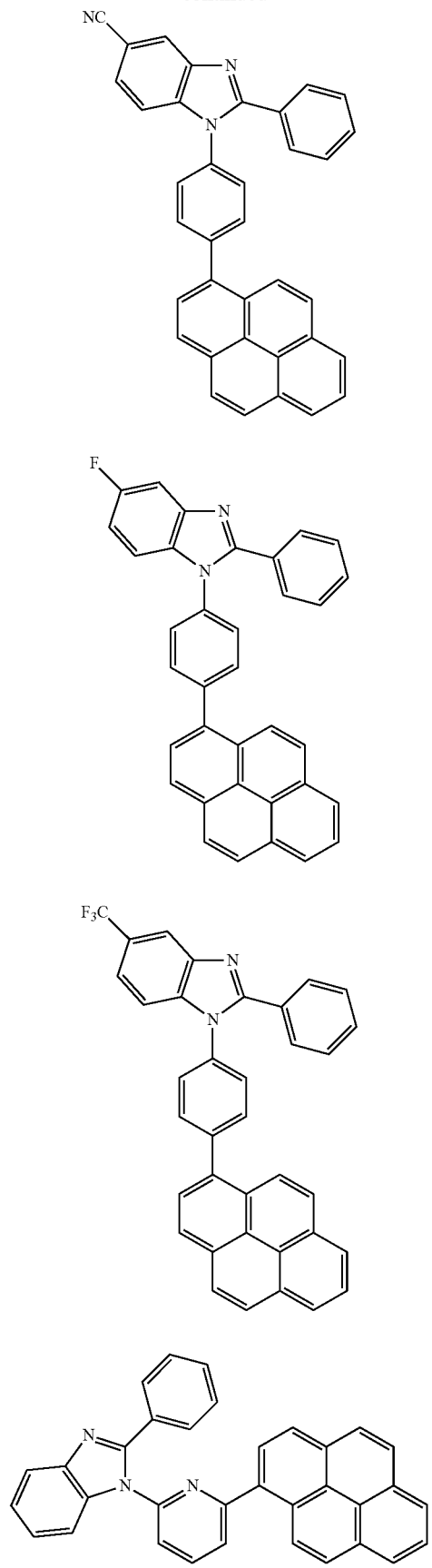 [SMILES: N#Cc1ccc2c(c1)nc(-c1ccccc1)n2-c1ccc(-c2ccc3ccc4cccc5ccc2c3c45)cc1 ; Fc1ccc2c(c1)nc(-c1ccccc1)n2-c1ccc(-c2ccc3ccc4cccc5ccc2c3c45)cc1 ; FC(F)(F)c1ccc2c(c1)nc(-c1ccccc1)n2-c1ccc(-c2ccc3ccc4cccc5ccc2c3c45)cc1 ; c1ccc(-c2nc3ccccc3n2-c2cccc(-c3ccc4ccc5cccc6ccc3c4c56)n2)cc1]

31
-continued
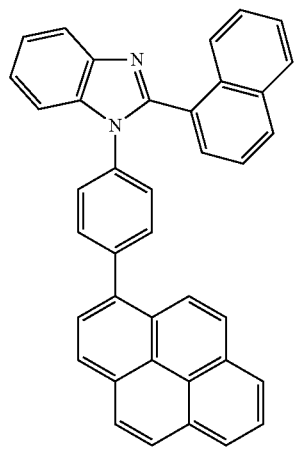
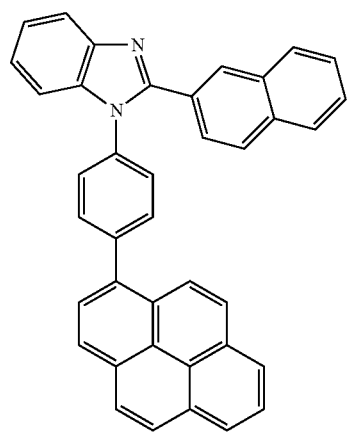
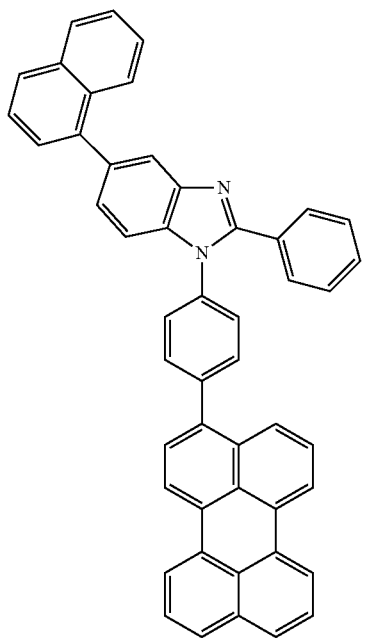
32
-continued
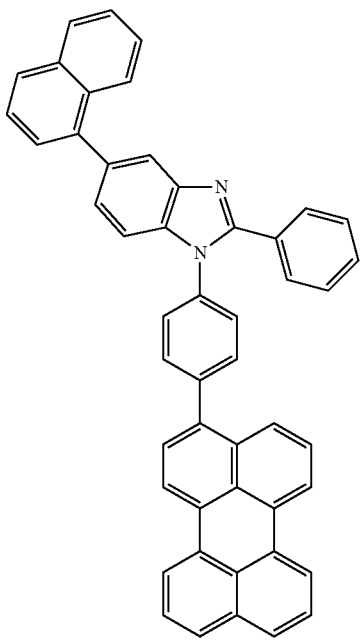
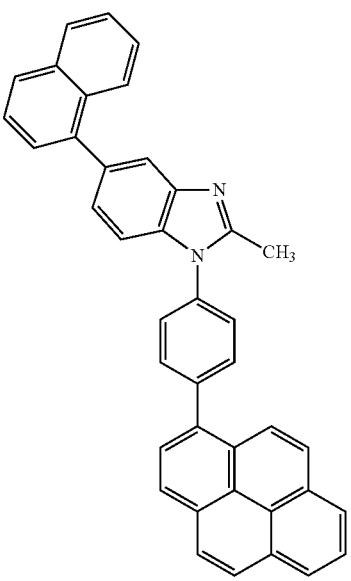

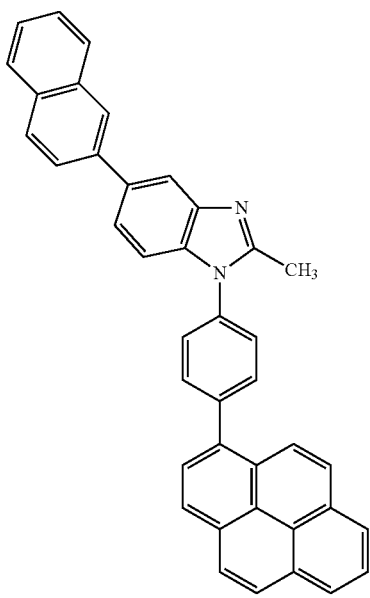 [SMILES: Cc1nc2cc(-c3ccc4ccccc4c3)ccc2n1-c1ccc(-c2ccc3ccc4cccc5ccc2c3c45)cc1]
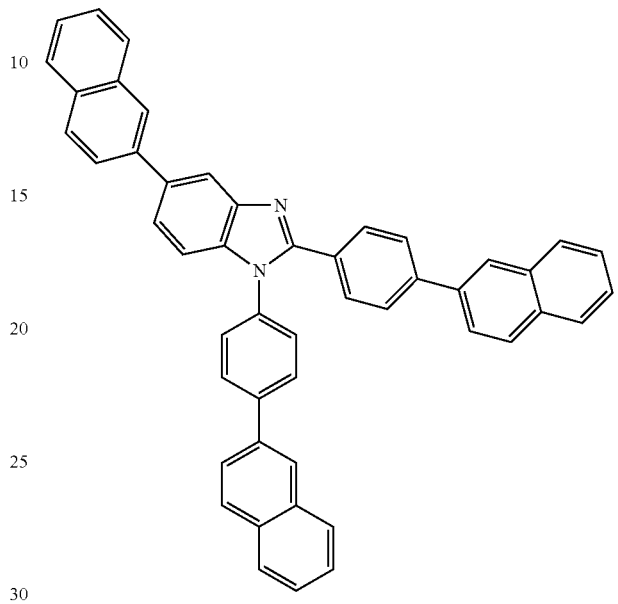
Examples of the nitrogen-containing heterocyclic derivative represented by formula (1b) are shown below, although not limited to the following exemplary compounds.
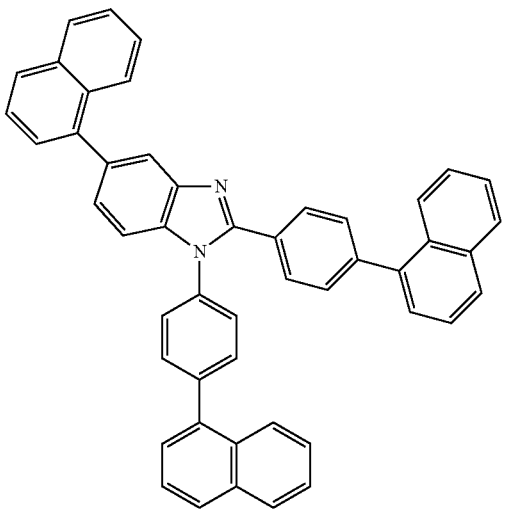
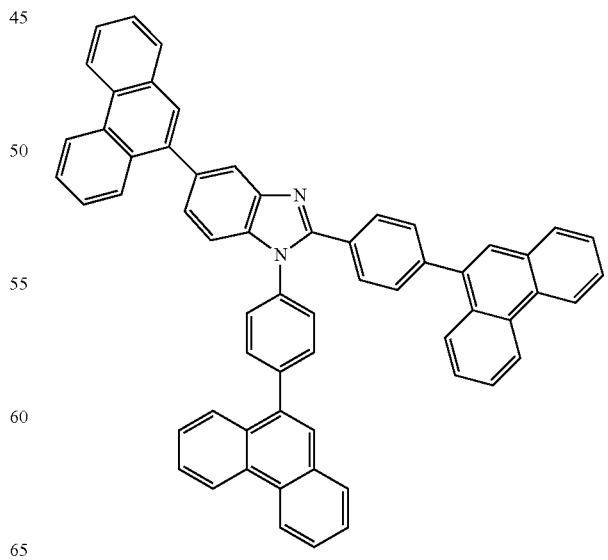

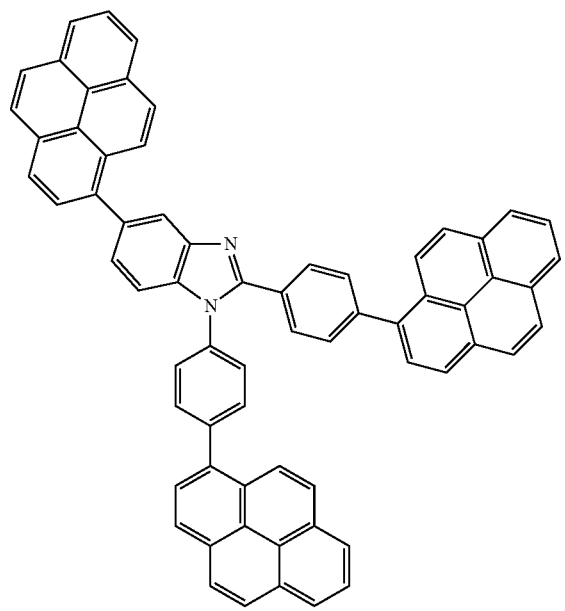
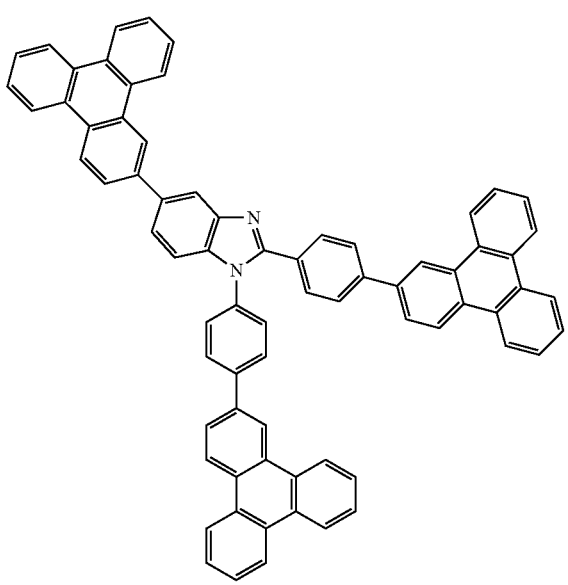
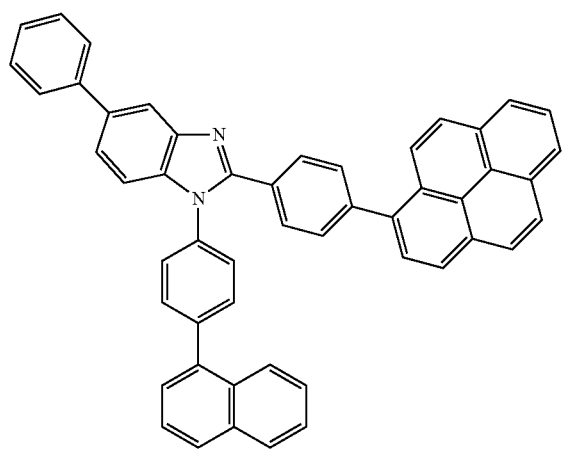
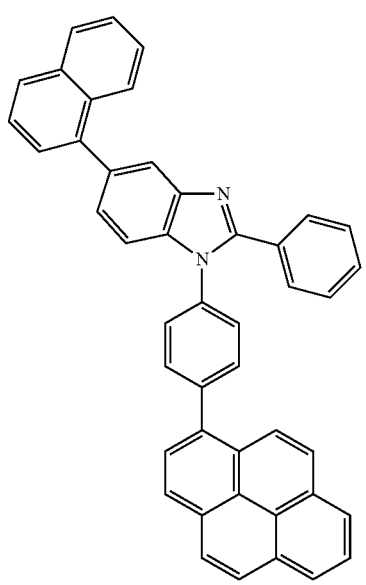
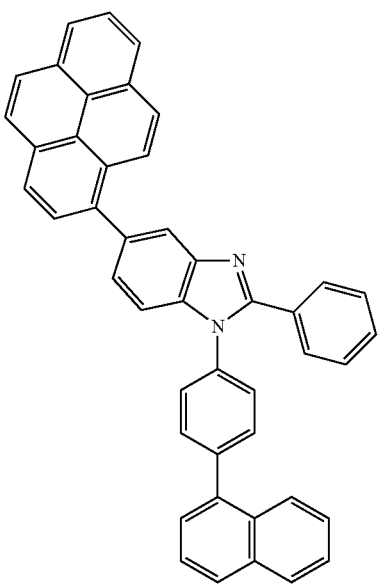
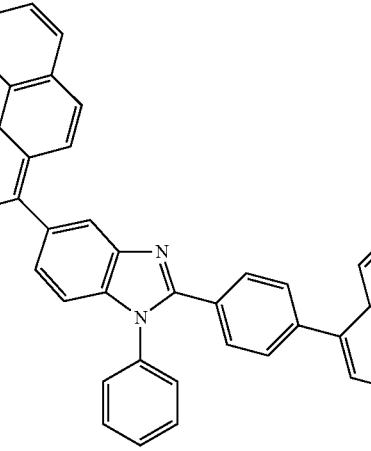

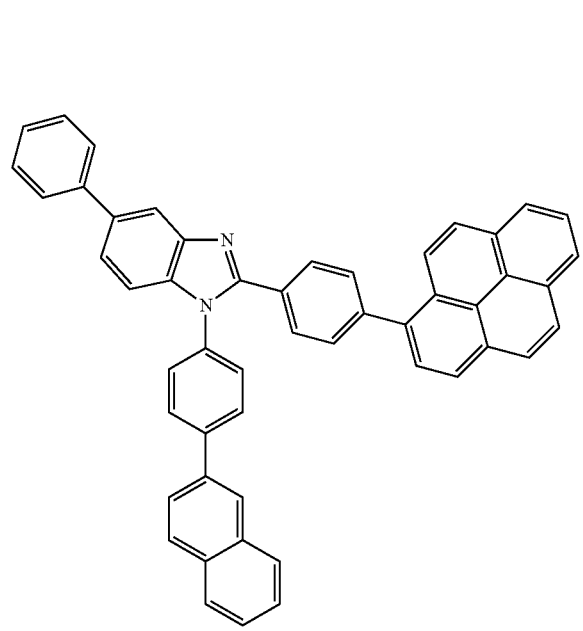
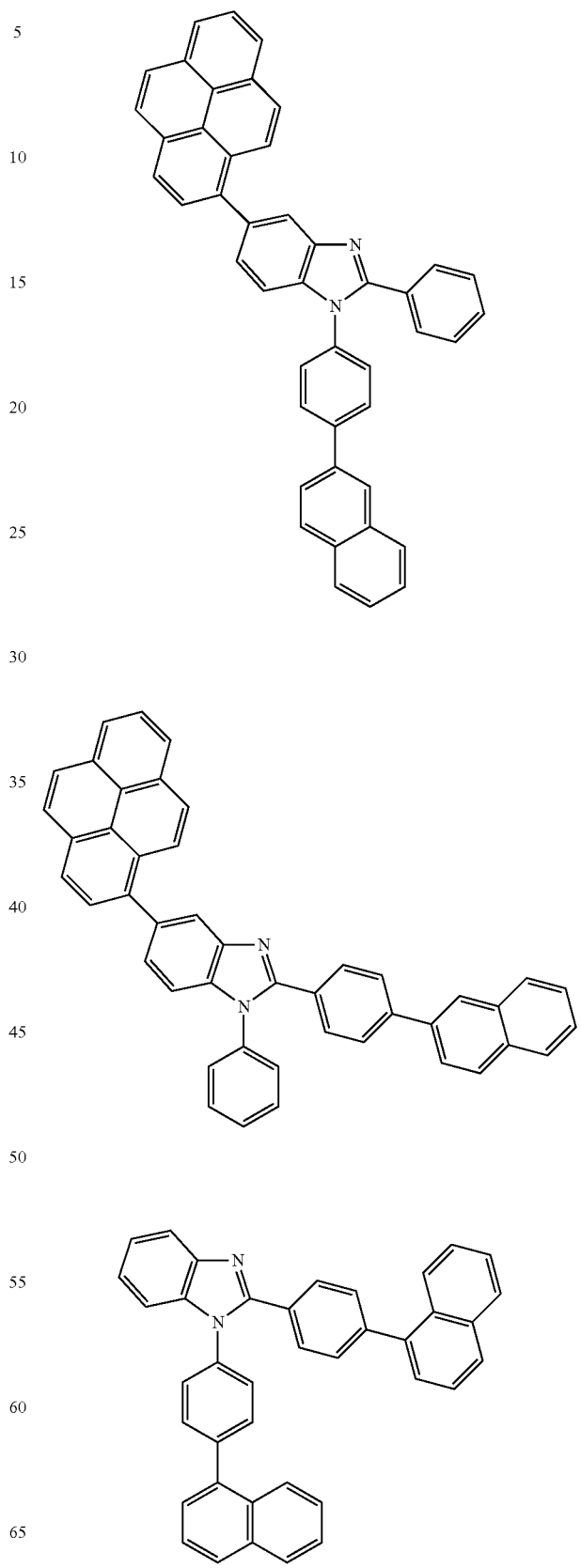

-continued
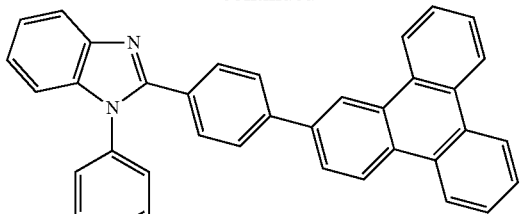
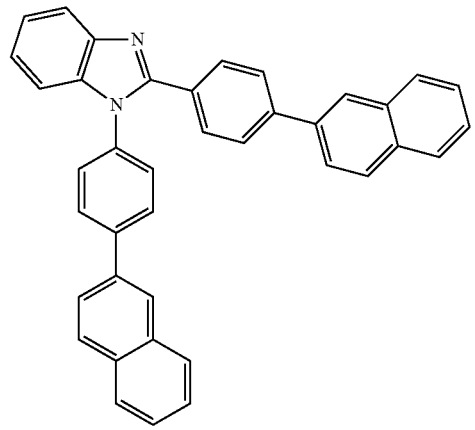
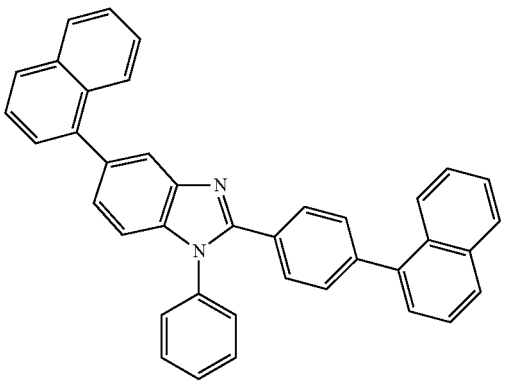
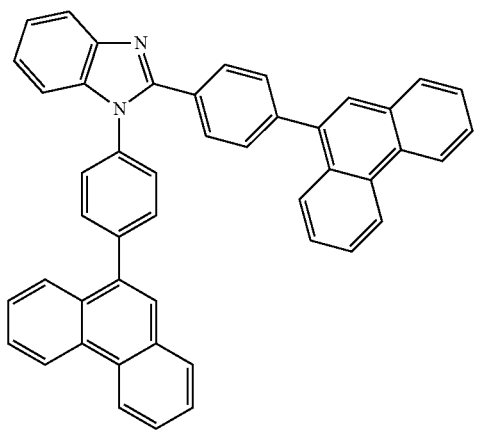
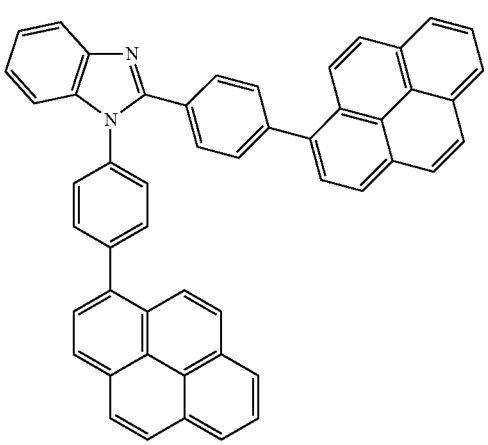

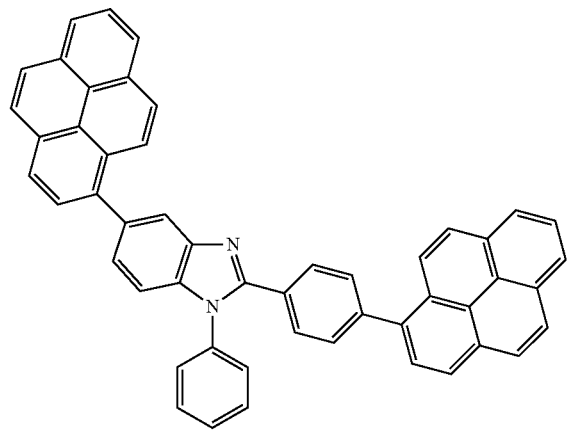
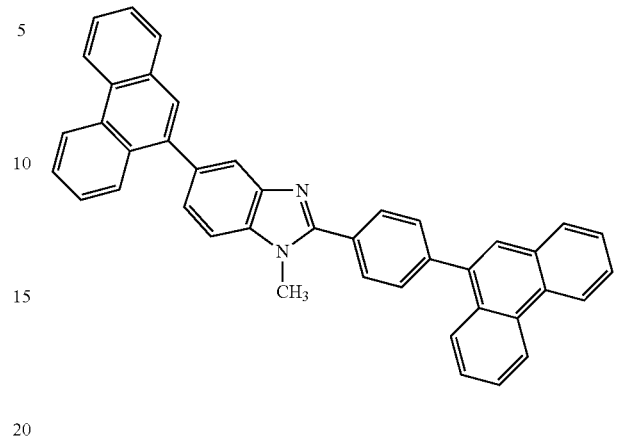
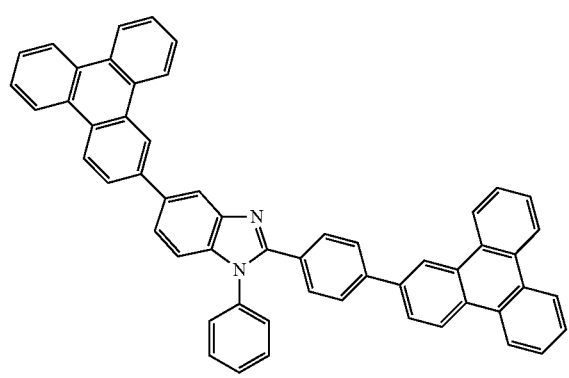
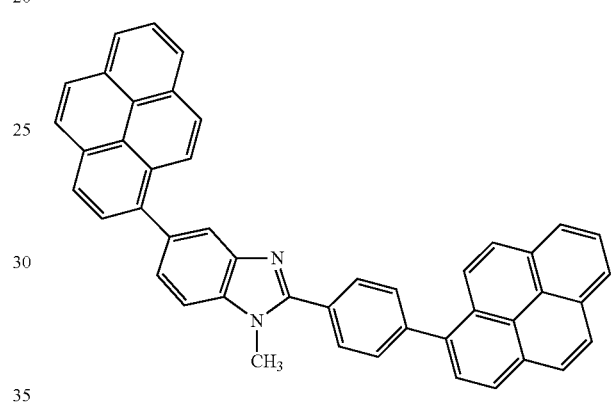
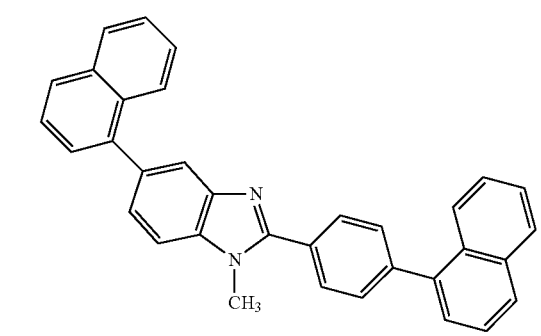
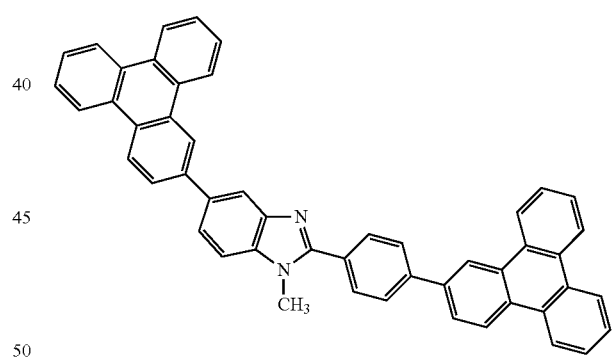
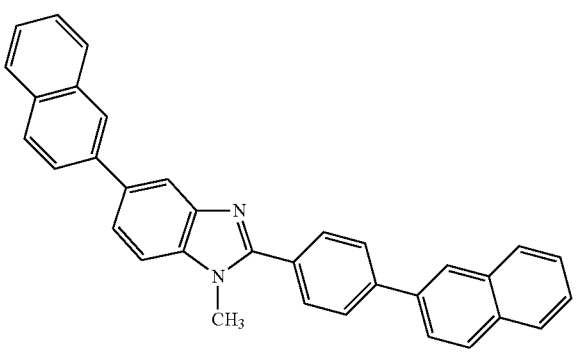
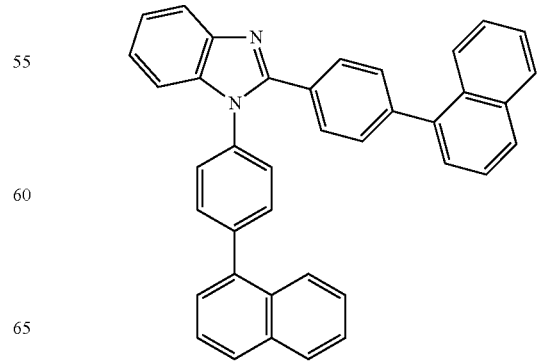

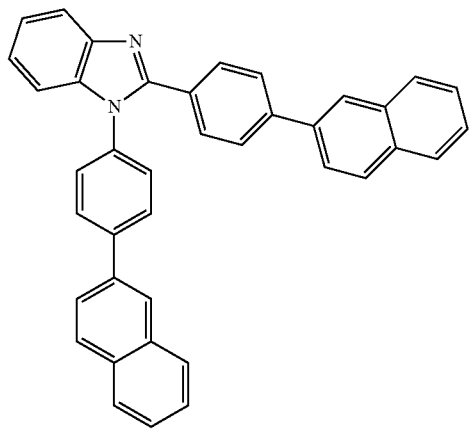
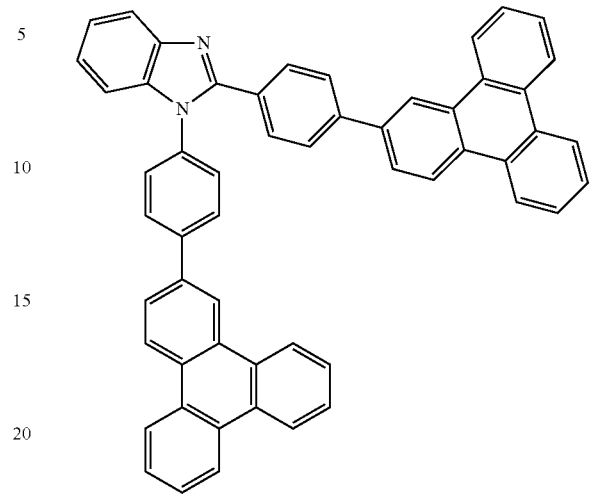
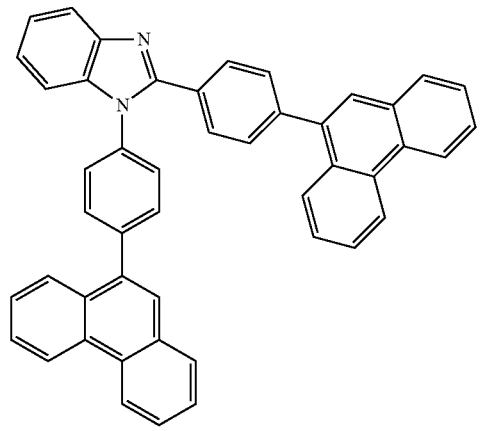
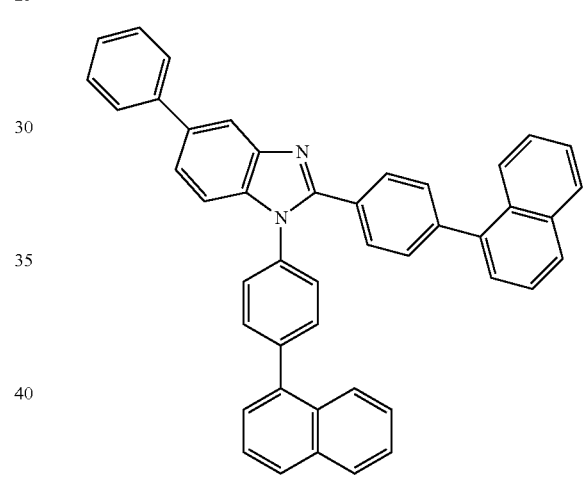
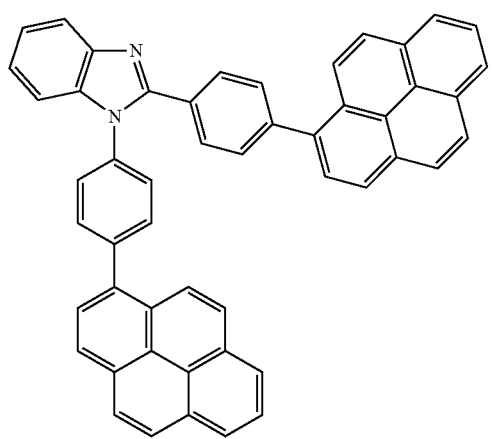
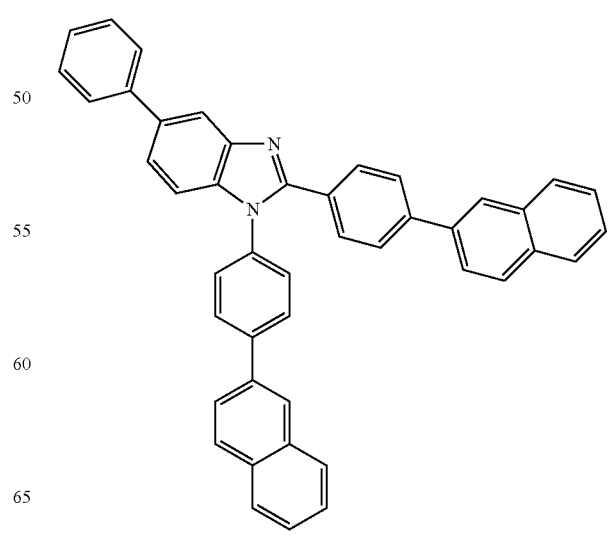

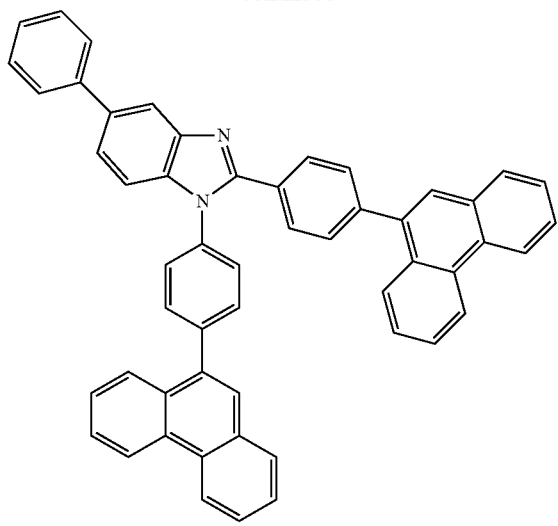
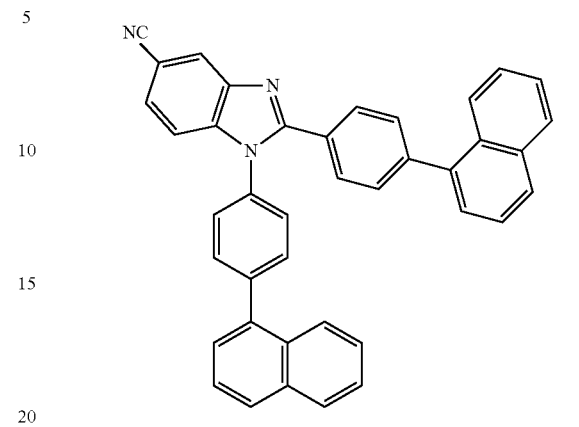
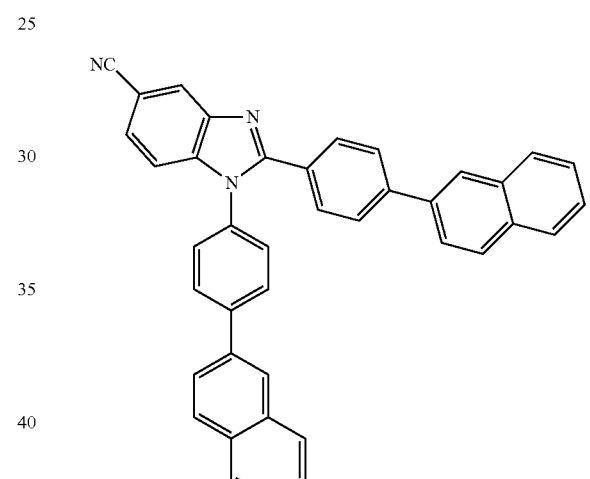
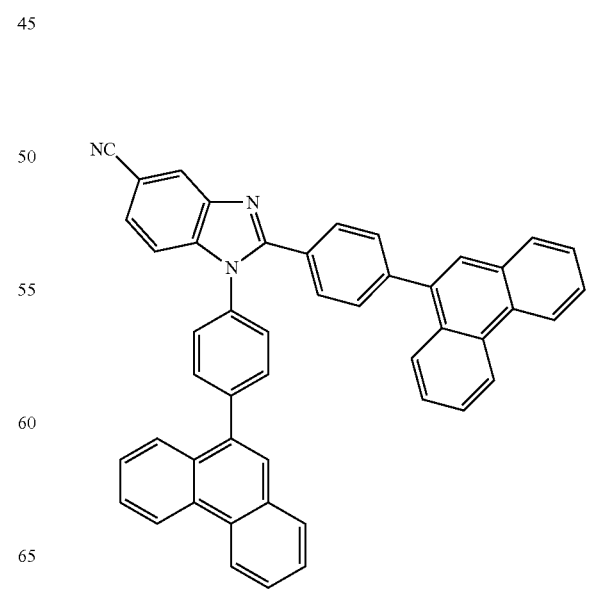

-continued
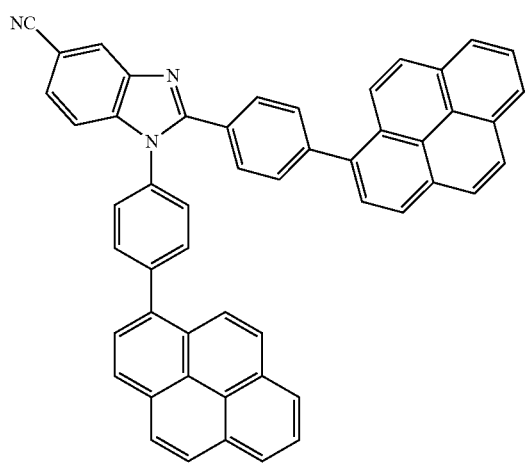
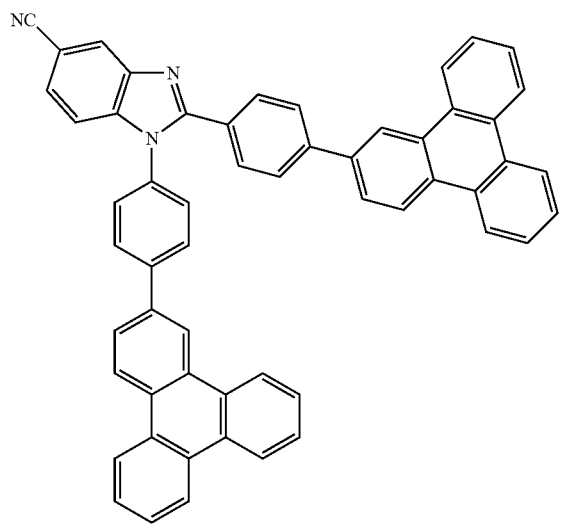
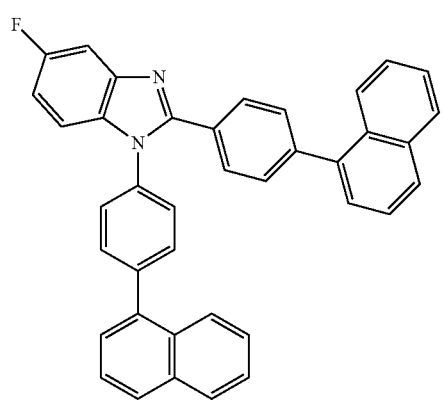
-continued
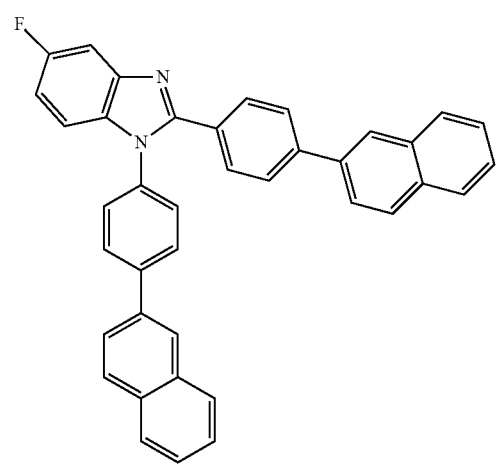
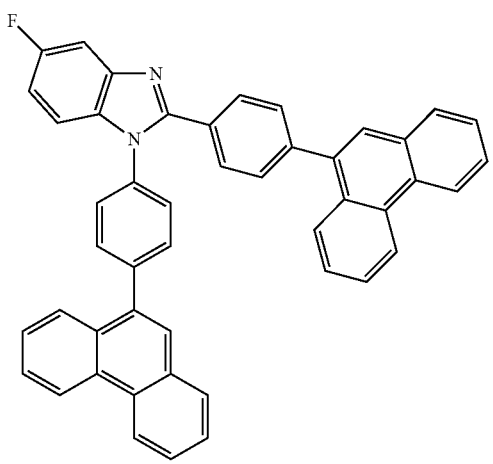
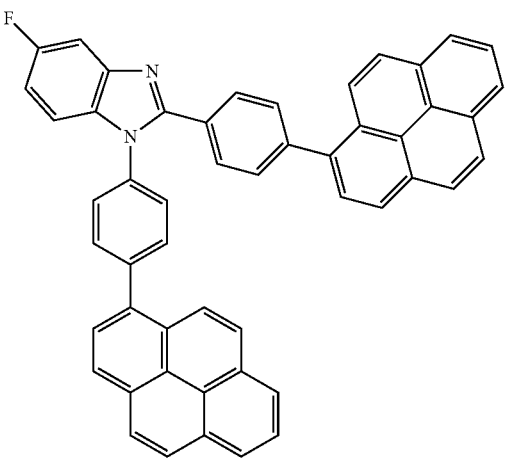

-continued

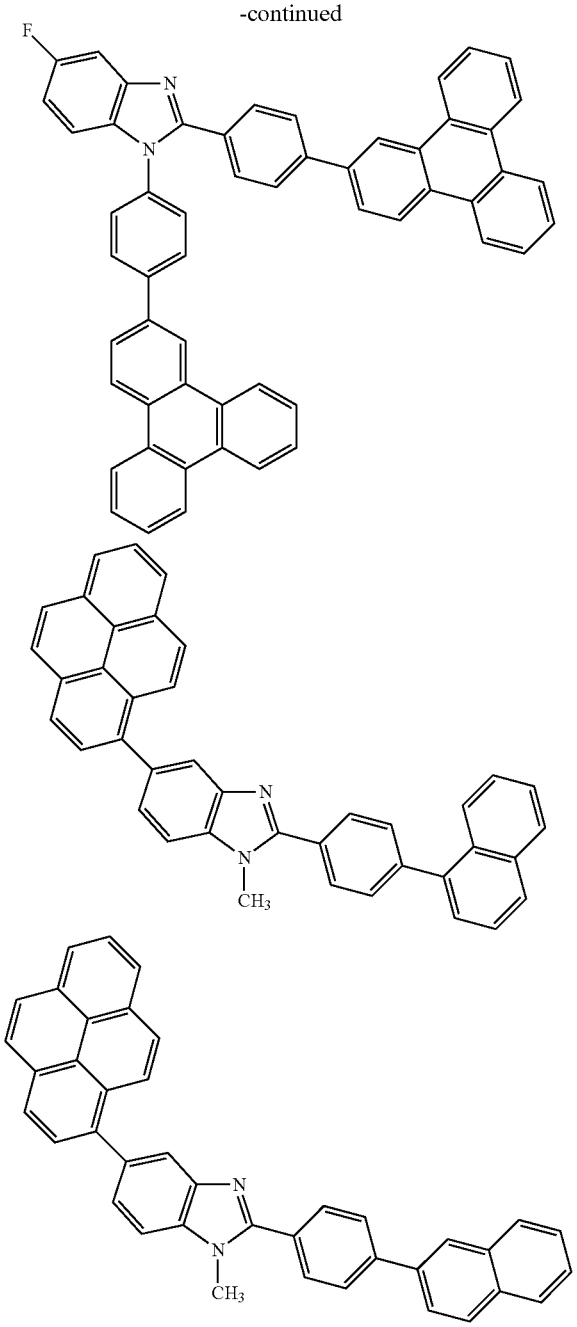

Next, the organic EL device of the invention will be described.

The organic EL device of the invention comprises an organic thin-film layer between a cathode and an anode. The organic thin-film layer comprises one or more layers having a light emitting layer. At least one layer of the organic thin-film layer comprises the nitrogen-containing heterocyclic derivative of the invention.

In a preferred embodiment of the invention, the organic thin-film layer includes an electron injecting layer or an electron transporting layer, and the electron injecting layer or the electron transporting layer contains the nitrogen-containing heterocyclic derivative of the invention. Preferably, the electron transporting layer contains the nitrogen-containing heterocyclic derivative, and more preferably, the electron injecting layer or the electron transporting layer further contains a reducing dopant.

In another preferred embodiment of the invention, the light emitting layer contains the nitrogen-containing heterocyclic derivative. In addition to the nitrogen-containing heterocyclic derivative, the light emitting layer may further contain at least one of a phosphorescent dopant and a fluorescent dopant. With such a dopant, the light emitting layer functions as a phosphorescent emitting layer and a fluorescent emitting layer.

Examples of the typical architecture of the organic EL devices include, but not particularly limited to,
(1) anode/light-emitting layer/cathode,
(2) anode/hole injecting layer/light-emitting layer/cathode,
(3) anode/light-emitting layer/electron injecting layer/cathode,
(4) anode/hole injecting layer/light-emitting layer/electron injecting layer/cathode,
(5) anode/organic semiconductor layer/light-emitting layer/cathode,
(6) anode/organic semiconductor layer/electron blocking layer/light-emitting layer/cathode,
(7) anode/organic semiconductor layer/light-emitting layer/adhesion improving layer/cathode,
(8) anode/hole injecting layer/hole transporting layer/light-emitting layer/electron injecting layer/cathode,
(9) anode/insulating layer/light-emitting layer/insulating layer/cathode,
(10) anode/inorganic semiconductor layer/insulating layer/light-emitting layer/insulating layer/cathode,
(11) anode/organic semiconductor layer/insulating layer/light-emitting layer/insulating layer/cathode,
(12) anode/insulating layer/hole injecting layer/hole transporting layer/light-emitting layer/insulating layer/cathode, and
(13) anode/insulating layer/hole injecting layer/hole transporting layer/light-emitting layer/electron injecting layer/cathode, with the device structure (8) being preferably used.

The nitrogen-containing heterocyclic derivative may be included in any layer of the organic thin-film layer of organic EL device, preferably in the emitting zone or the electron transporting zone, and particularly preferably in the electron injecting layer, the electron transporting layer and the light emitting layer.

The architecture (8) is shown in FIG. 1. The organic EL device 1 is constructed by a cathode 10 and an anode 20, and further a hole injecting layer 31, a hole transporting layer 32, a light emitting layer 33, and an electron injecting layer 34 which are interposed between the cathode and the anode. The hole injecting layer 31, the hole transporting layer 32, the light emitting layer 33, and the electron injecting layer 34 constitute two or more layers of the organic thin-film layer. At least one layer of the organic thin-film layer 31 to 34 contains the nitrogen-containing heterocyclic derivative of the invention.

Each part of the organic EL device will be described below.

The organic EL device is generally formed on a substrate for support the organic EL device. The substrate is preferably flat. When allowing the emitted light to pass through the substrate, a light-transmissive substrate having a transmittance of 50% or more to 400-700 nm visible lights is preferably used.

Examples of the light-transmissive substrate include those made from soda-lime glass, barium-strontium-containing glass, lead glass, aluminosilicate glass, borosilicate glass, barium borosilicate glass, or quartz. Examples of the synthetic resin plate include those made from polycarbonate resin, acrylic resin, polyethylene terephthalate resin, polyether sulfide resin or polysulfone resin.

The anode injects holes into a hole injecting layer, a hole transporting layer or a light emitting layer and it is effective to have a work function of 4.5 eV or more. Examples of the anode material include indium tin oxide (ITO), mixture of indium oxide and zinc oxide (IZO), mixture of ITO and cerium oxide (ITCO), mixture of IZO and cerium oxide (IZCO), mixture of indium oxide and cerium oxide (ICO), mixture of zinc oxide and aluminum oxide (AZO), tin oxide (NESA), gold, silver, platinum and copper. The anode is formed by a vapor deposition method or a sputtering method.

When the light emitted from the light emitting layer is allowed to pass through the anode, the transmittance of the anode to the emitted light is preferably 10% or more. The sheet resistance of the anode is preferably several hundreds $\Omega/\square$ or less. The thickness of the anode varies depending upon the kind of material and generally 10 nm to 1 μm, preferably 50 to 200 nm.

The light emitting layer has the following functions:

(i) Injection function: function of injecting holes from the anode or hole injecting layer, and injecting electrons from the cathode or electron injecting layer, due to the action of electric field;

(ii) Transporting function: function of transporting the injected charges (holes and electrons) by the force of electric field; and (iii) Emission function: function of providing a zone for recombination of electrons and holes to cause the emission.

The light emitting layer is formed by a known method such as a vapor deposition method, a spin coating method and LB method. The light emitting layer is particularly preferably a molecular deposit film. The molecular deposit film is a film formed by depositing a material compound in a gas phase or a film formed by solidifying a material in a solution or liquid phase. In general, the molecular deposit film can be distinguished from the thin film formed by LB method (molecular accumulation film) based on the differences in the aggregation structure and higher order structures and the differences in the function caused by these structural differences. The light emitting layer can be formed also by dissolving a binder such as a resin and the material in a solvent to prepare a solution and making the solution into a thin film by a spin coating method, etc.

Examples of the light emitting material or doping material usable for the light emitting layer includes, but not limited to, anthracene, naphthalene, phenanthrene, pyrene, tetracene, coronene, chrysene, fluorescein, perylene, phthaloperylene, naphthaloperylene, perinone, phthaloperinone, nap hthaloperinone, diphenylbutadiene, tetraphenylbutadiene, coumarin, oxadiazole, aldazine, bisbenzoxazoline, bisstyryl, pyrazine, cyclopentadiene, quinoline metal complex, aminoquinoline metal complex, benzoquinoline metal complex, imine, diphenylethylene, vinylanthracene, diaminecarbazol, pyran, thiopyran, polymethyne, merocyanine, imidazol chelate oxinoid compound, quinacridone, rubrene, derivatives thereof, and fluorescent dye.

Examples of the host material for use in the light emitting layer include the compounds represented by formulae (i) to (ix).

An asymmetric anthracene represented by formula (i):

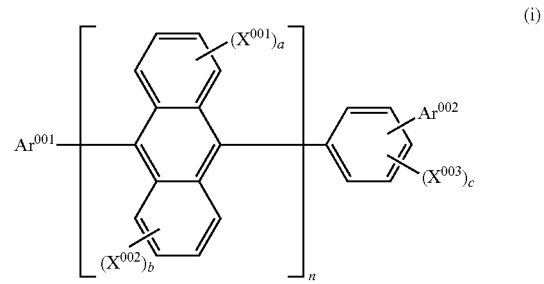

wherein $Ar^{001}$ is a substituted or unsubstituted condensed aromatic group having 10 to 50 ring-forming carbon atoms; $Ar^{002}$ is a substituted or unsubstituted aromatic group having 6 to 50 ring-forming carbon atoms; $X^{001}$ to $X^{003}$ are each independently a substituted or unsubstituted aromatic group having 6 to 50 ring-forming carbon atoms, a substituted or unsubstituted aromatic heterocyclic group having 5 to 50 ring-forming atoms, a substituted or unsubstituted alkyl group having 1 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring-forming carbon atoms, a substituted or unsubstituted arylthio group having 6 to 50 ring-forming carbon atoms, a substituted or unsubstituted alkoxycarbonyl group having 2 to 50 carbon atoms, carboxyl group, a halogen atom, cyano group, nitro group, or hydroxy group; a, b and c are each an integer of 0 to 4; n is an integer of 1 to 3, and when n is 2 or more, the groups in [ ] may be the same or different.

An asymmetric monoanthracene derivative represented by formula (ii):

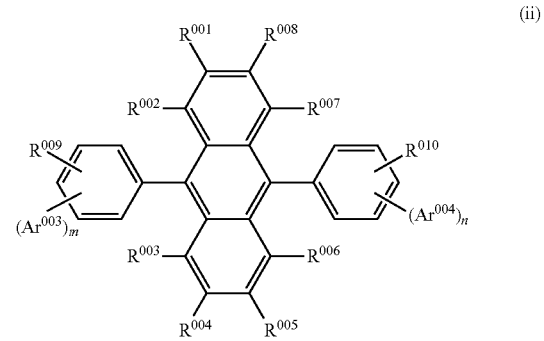

wherein $Ar^{003}$ and $Ar^{004}$ are each independently a substituted or unsubstituted aromatic ring group having 6 to 50 ring-forming carbon atoms; m and n are each an integer of 1 to 4, with the proviso that when m=n=1 and the bonding positions of $Ar^{003}$ and $Ar^{004}$ to the benzene rings are bilaterally symmetric to each other, $Ar^{003}$ is different from $Ar^{004}$, and when m or n is an integer of 2 to 4, m is different from n; and $R^{001}$ to $R^{010}$ are each independently hydrogen atom, a substituted or unsubstituted aromatic ring group having 6 to 50 ring-forming carbon atoms, a substituted or unsubstituted aromatic heterocyclic group having 5 to 50 ring-forming atoms, a substituted or unsubstituted alkyl group having 1 to 50 carbon atoms, a substituted or unsubstituted cycloalkyl group having 3 to 50 ring-forming carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring-forming carbon atoms, a substituted or unsubstituted arylthio group having 6 to 50 ring-forming carbon atoms, a substituted or unsubstituted alkoxycarbonyl group having 2 to 50 carbon atoms, a substituted or unsubstituted silyl group, carboxyl group, a halogen atom, cyano group, nitro group, or hydroxy group.

An asymmetric pyrene derivative represented by formula (iii):

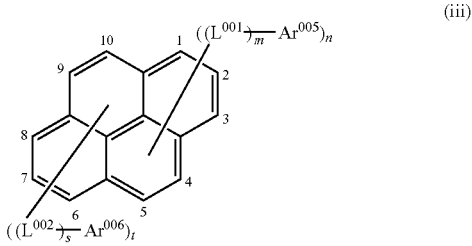

wherein $Ar^{005}$ and $Ar^{006}$ are each a substituted or unsubstituted aromatic group having 6 to 50 ring-forming carbon atoms;

$L^{001}$ and $L^{002}$ are each a substituted or unsubstituted phenylene group, a substituted or unsubstituted naphthanylene group, a substituted or unsubstituted fluorenylene group, or a substituted or unsubstituted dibenzosilolylene group; and m is an integer of 0 to 2, n is an integer of 1 to 4, s is an integer of 0 to 2, and t is an integer of 0 to 4.

An asymmetric anthracene derivative represented by formula (iv):

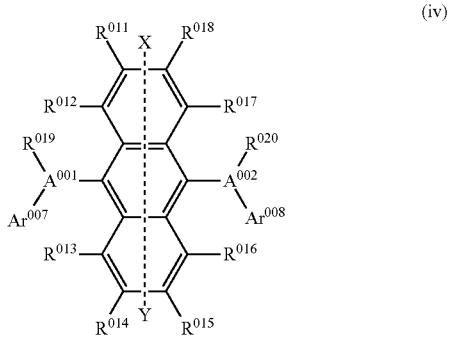

wherein $A^{001}$ and $A^{002}$ are each independently a substituted or unsubstituted condensed aromatic ring group having 10 to 20 ring-forming carbon atoms;

$Ar^{007}$ and $Ar^{008}$ are each independently hydrogen atom or a substituted or unsubstituted aromatic ring group having 6 to 50 ring-forming carbon atoms;

$R^{011}$ to $R^{020}$ are each independently hydrogen atom, a substituted or unsubstituted aromatic ring group having 6 to 50 ring-forming carbon atoms, a substituted or unsubstituted aromatic heterocyclic group having 5 to 50 ring-forming atoms, a substituted or unsubstituted alkyl group having 1 to 50 carbon atoms, a substituted or unsubstituted cycloalkyl group having 3 to 50 ring-forming carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring-forming carbon atoms, a substituted or unsubstituted arylthio group having 6 to 50 ring-forming carbon atoms, a substituted or unsubstituted alkoxycarbonyl group having 2 to 50 carbon atoms, a substituted or unsubstituted silyl group, carboxyl group, a halogen atom, cyano group, nitro group, or hydroxy group; and $Ar^{007}$, $Ar^{008}$, $R^{019}$ and $R^{020}$ are each may be two or more groups and adjacent pair of groups may form a saturated or unsaturated ring structure.

An anthracene derivative represented by formula (v):

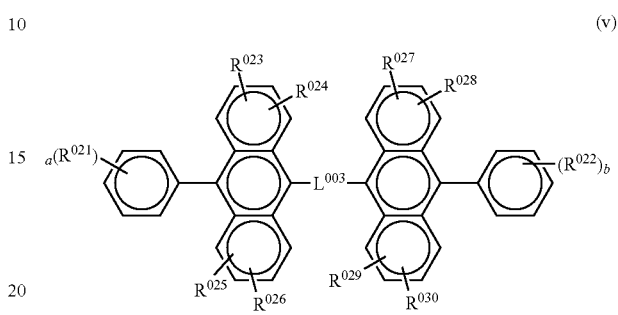

wherein $R^{021}$ to $R^{030}$ are each independently hydrogen atom, a substituted or unsubstituted alkyl group having 1 to 50 carbon atoms, a substituted or unsubstituted cycloalkyl group having 3 to 50 ring-forming carbon atoms, a substituted or unsubstituted aryl group having 6 to 50 ring-forming carbon atoms, a substituted or unsubstituted alkoxyl group having 1 to 50 carbon atoms, a substituted or unsubstituted aryloxy group having 6 to 50 ring-forming carbon atoms, a substituted or unsubstituted alkylamino group having 1 to 50 carbon atoms, a substituted or unsubstituted alkenyl group having 2 to 50 carbon atoms, a substituted or unsubstituted arylamino group having 6 to 50 ring-forming carbon atoms, or a substituted or unsubstituted heterocyclic group having 5 to 50 ring-forming atoms; a and b are each an integer of 1 to 5, when a and b are 2 or more, $R^{021}$ groups and $R^{022}$ groups may be the same or different, respectively, and $R^{021}$ groups and $R^{022}$ groups may be bonded to form a ring, and $R^{023}$ and $R^{024}$, $R^{025}$ and $R^{026}$, $R^{027}$ and $R^{028}$, and $R^{029}$ and $R^{030}$ may be bonded to form a ring; $L^{003}$ is a single bond, —O—, —S—, —N(R)— wherein R is a substituted or unsubstituted alkyl group having 1 to 50 carbon atoms or a substituted or unsubstituted aryl group having 6 to 50 ring-forming carbon atoms, a substituted or unsubstituted alkylene group having 1 to 50 carbon atoms, or a substituted or unsubstituted arylene group having 6 to 50 ring-forming carbon atoms.

An anthracene derivative represented by formula (vi):

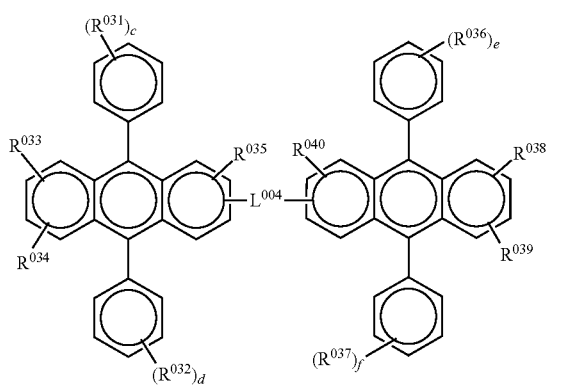

wherein $R^{031}$ to $R^{040}$ are each independently hydrogen atom, a substituted or unsubstituted alkyl group having 1 to 50 carbon atoms, a substituted or unsubstituted cycloalkyl group having 3 to 50 ring-forming carbon atoms, a substituted or unsubstituted aryl group having 6 to 50 ring-forming carbon atoms, a substituted or unsubstituted alkoxyl group having 1 to 50 carbon atoms, a substituted or unsubstituted aryloxy group having 6 to 50 ring-forming carbon atoms, a substituted or unsubstituted alkylamino group having 1 to 50 carbon atoms, a substituted or unsubstituted arylamino group having 6 to 50 ring-forming carbon atoms, or a substituted or unsubstituted heterocyclic group having 5 to 50 ring-forming atoms; c, d, e and f are each an integer of 1 to 5, when c, d, e and f are 2 or more, $R^{031}$ groups, $R^{032}$ groups, $R^{036}$ groups and $R^{037}$ groups may be the same or different, respectively, and $R^{031}$ groups, $R^{032}$ groups, $R^{036}$ groups and $R^{037}$ groups maybe bonded to form a ring, and $R^{033}$ and $R^{034}$ and $R^{038}$ and $R^{039}$ may be bonded to form a ring; and $L^{004}$ is a single bond, —O—, —S—, —N(R)— wherein R is a substituted or unsubstituted alkyl group having 1 to 50 carbon atoms or a substituted or unsubstituted aryl group having 6 to 50 ring-forming carbon atoms, a substituted or unsubstituted alkylene group having 1 to 50 carbon atoms, or a substituted or unsubstituted arylene group having 6 to 50 ring-forming carbon atoms.

A spirofluorene derivative represented by formula (vii):

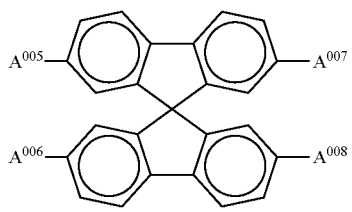

(vii)

wherein $A^{005}$ to $A^{008}$ are each independently a substituted or unsubstituted biphenylyl group or a substituted or unsubstituted naphthyl group.

A condensed ring-containing compound represented by formula (viii);

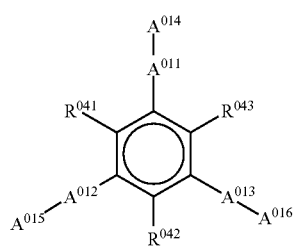

(viii)

wherein $A^{011}$ to $A^{013}$ are each independently a substituted or unsubstituted arylene group having 6 to 50 ring-forming carbon atoms; $A^{014}$ to $A^{016}$ are each independently hydrogen atom or a substituted or unsubstituted aryl group having 6 to 50 ring-forming carbon atoms; $R^{041}$ to $R^{043}$ are each independently hydrogen atom, an alkyl group having 1 to 6 carbon atoms, a cycloalkyl group having 3 to 6 carbon atoms, an alkoxyl group having 1 to 6 carbon atoms, an aryloxy group having 6 to 18 ring-forming carbon atoms, an aralkyloxy group having 7 to 18 carbon atoms, an arylamino group having 6 to 16 ring-forming carbon atoms, nitro group, cyano group, an ester group having 2 to 6 carbon atoms, or a halogen atom; and at least one of $A^{011}$ to $A^{016}$ is a tri- or more cyclic condensed aromatic group.

A fluorene compound represented by formula (ix):

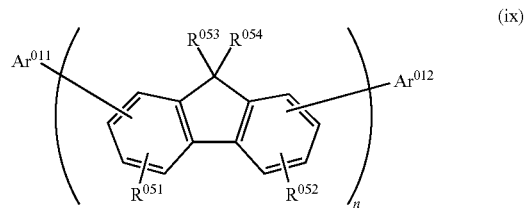

(ix)

wherein $R^{051}$ and $R^{052}$ are each hydrogen atom, a substituted or unsubstituted alkyl group having 1 to 50 carbon atoms, a substituted or unsubstituted aralkyl group having 7 to 50 carbon atoms, a substituted or unsubstituted aryl group having 6 to 50 ring-forming carbon atoms, a substituted or unsubstituted heterocyclic group having 5 to 50 ring-forming atoms, a substituted or unsubstituted amino group having 1 to 50 carbon atoms, cyano group, or a halogen atom; $R^{051}$ groups and $R^{052}$ group bonding to different fluorene groups may be the same or different; $R^{051}$ and $R^{052}$ bonding to the same fluorene group may be the same or different; $R^{053}$ and $R^{054}$ are each hydrogen atom, a substituted or unsubstituted alkyl group having 1 to 50 carbon atoms, a substituted or unsubstituted aralkyl group having 7 to 50 carbon atoms, a substituted or unsubstituted aryl group having 6 to 50 ring-forming carbon atoms, or a substituted or unsubstituted heterocyclic group having 5 to 50 ring-forming atoms; $R^{053}$ groups and $R^{054}$ groups bonding to different fluorene groups may be the same or different; $R^{053}$ and $R^{054}$ bonding to the same fluorene group may be the same or different; $Ar^{011}$ and $Ar^{012}$ are each a substituted or unsubstituted condensed polycyclic aromatic group having 3 or more benzene rings or a substituted or unsubstituted condensed polycyclic heterocyclic group having a benzene ring and a hetero ring three or more in total and bonding to the fluorene group via carbon; $Ar^{011}$ and $Ar^{012}$ may be the same or different; and n is an integer of 1 to 10.

In the organic EL device of the invention, the light emitting layer may contain, in addition to the light emitting material of the invention, a phosphorescent dopant and/or a fluorescent dopant, if necessary. Alternatively, a light emitting layer containing such a dopant may be laminated onto the light emitting layer containing the compound of the invention.

The phosphorescent dopant is a compound capable of emitting light from the triplet excimer. The phosphorescent dopant is not limited as long as light is emitted from the triplet excimer, and is preferably a metal complex having at least one metal selected from Ir, Ru, Pd, Os and Re and more preferably a porphyrin metal complex and an orthometalated metal complex. The phosphorescent dopant may be used singly or in combination of two or more.

As the porphyrin metal complex, porphyrin platinum complexes are preferable.

The ligand forming the orthometalated complex may include various kinds of ligands. Preferred ligand may include a compound having a phenylpyridine residue, bipyridyl residue or phenanthroline residue, a 2-phenylpyridine derivative, a 7,8-benzoquinoline derivative, a 2-(2-thienyl) pyridine derivative, a 2-(1-naphthyl)pyridine derivative, and a 2-phenylquinoline derivative. These ligands may have a substituent, if necessary. In particular, a fluorinated ligand and a trifluoromethyl-substituted ligand are preferable as the blue-emitting dopant. Ligands other than those described above such as acetylacetonato and picric acid may be used as an ancillary ligand.

Examples of the metal complex include tris(2-phenylpyridine)iridium, tris(2-phenylpyridine)ruthenium, tris(2-phenylpyridine)palladium, bis(2-phenylpyridine)platinum, tris(2-phenylpyridine)osmium, tris(2-phenylpyridine)rhenium, octaethylplatinum porphyrin, octaphenylplatinum porphyrin, octaethylpalladium porphyrin, and octaphenylpalladium porphyrin. The metal complex is not particularly limited to those mentioned above and suitably selected according to a desired emission color, a desired device performance and a host compound to be used.

The content of the phosphorescent dopant in the light emitting layer is not particularly limited and is suitably selected according to the desirability. The content is, for example, 0.1 to 70% by mass and preferably 1 to 30% by mass. If less than 0.1% by mass, the light emission is weak and the effect of using the dopant is not obtained. If exceeding 70% by mass, the phenomenon called concentration quenching arises markedly and the property of the device may deteriorate.

The fluorescent dopant is preferably selected from an amine compound, an aromatic compound, a chelate complex such as tris(8-quinolinolato)aluminum, a coumarin derivative, a tetraphenylbutadiene derivative, a bisstyrylarylene derivative, and an oxadiazolederivative according to a desired emission color, with a styrylamine compound, a styryldiamine compound, an arylamine compound, and an aryldiamine compound being more preferred. A condensed polycyclic aromatic compound not an amine compound is also preferable. These fluorescent dopants may be used alone or in combination of two or more.

The styrylamine compound and the styryldiamine compound are preferably represented by formula (A):

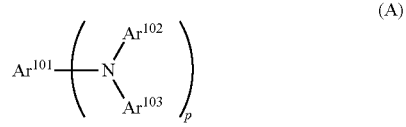

(A)

wherein $Ar^{101}$ is a p-valent group derived from benzene, naphthalene, biphenyl, terphenyl, stilbene, or distyrylaryl; $Ar^{102}$ and $Ar^{103}$ are each an aromatic hydrocarbon group having 6 to 20 carbon atoms; $Ar^{101}$, $Ar^{102}$ and $Ar^{103}$ may be substituted, at least one of $Ar^{101}$ to $Ar^{103}$ is substituted by a styryl group, and more preferably at least one of $Ar^{102}$ and $Ar^{103}$ is substituted by a styryl group; and p is an integer of 1 to 4, preferably an integer of 1 to 2.

Examples of the aromatic hydrocarbon group having 6 to 20 carbon atoms include phenyl group, naphthyl group, anthranyl group, phenanthryl group, and terphenyl group.

The arylamine compound and the aryldiamine compound are preferably represented by formula (B):

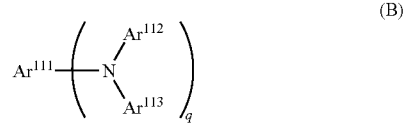

(B)

wherein $Ar^{111}$ is a q-valent, substituted or unsubstituted aryl group having 6 to 40 ring-forming carbon atoms or a q-valent, substituted or unsubstituted heteroaryl group having 5 to 40 ring-forming atoms; $Ar^{112}$ and $Ar^{113}$ are each a substituted or unsubstituted aryl group having 6 to 40 ring-forming carbon atoms or a substituted or unsubstituted heteroaryl group having 5 to 40 ring-forming atoms; and q is an integer of 1 to 4, preferably an integer of 1 to 2.

Examples of the aryl group and the heteroaryl group include phenyl group, naphthyl group, anthranyl group, phenanthryl group, pyrenyl group, coronyl group, biphenyl group, terphenyl group, pyrrolyl group, furanyl group, thiophenyl group, benzothiophenyl group, oxadiazolyl group, diphenylanthranyl group, indolyl group, carbazolyl group, pyridyl group, benzoquinolyl group, fluoranthenyl group, acenaphthofluoranthenyl group, stilbene group, perylenyl group, chrysenyl group, picenyl group, triphenylennl group, rubicenyl group, benzoanthracenyl group, phenylanthranyl group, and bisanthracenyl group, with naphthyl group, anthranyl group, chrysenyl group, and pyrenyl group being preferred.

Examples of preferred substituent for the aryl group and the heteroaryl group include an alkyl group having 1 to 6 carbon atoms (ethyl group, methyl group, isopropyl group, n-propyl group, s-butyl group, t-butyl group, pentyl group, hexyl group, etc.), a cycloalkyl group having 3 to 6 carbon atoms (cyclopentyl group, cyclohexyl group, etc.), an alkoxy group having 1 to 6 carbon atoms (ethoxy group, methoxy group, isopropoxy group, n-propoxy group, s-butoxy group, t-butoxy group, pentoxy group, hexyloxy group, etc.), a cycloalkoxy group having 3 to 6 carbon atoms (cyclopentoxy group, cyclohexyloxy group, etc.), an aryl group having 6 to 40 ring-forming carbon atoms, an amino group substituted by an aryl group having 6 to 40 ring-forming carbon atoms, an ester group having an aryl group having 6 to 40 ring-forming carbon atoms, an ester group having an alkyl group having 1 to 6 carbon atoms, cyano group, nitro group, and a halogen atom.

The light emitting layer may further comprise a hole transporting material, an electron transporting material and a polymer binder, if necessary. The thickness of the light emitting layer is preferably 5 to 50 nm, more preferably 7 to 50 nm and most preferably 10 to 50 nm. If less than 5 nm, the formation of the light emitting layer is difficult and the adjustment of chromaticity is difficult. If exceeding 50 nm, the driving voltage is likely to increase.

The hole injecting layer and the hole transporting layer facilitate the injection of holes into the light emitting layer and transport holes to the light emitting zone. These layers have a large hole mobility and an ionization energy as small as 5.5 eV or less. A material capable of transporting holes to the light emitting layer under a low electric field strength is preferred for the hole injecting layer and the hole transporting layer, and the material preferably has a hole mobility of, for example, $10^{-4}$ cm$^2$/V·s or more under an electric field of $10^4$ to $10^6$ V/cm.

The material for the hole injecting layer and the hole transporting layer is not particularly limited and is selected from the materials commonly used as the hole transporting material in the filed of photoconductive material and the materials used in the hole injecting layer and the hole transporting layer of known organic EL devices.

The hole injecting layer and the hole transporting layer may contain the following aromatic amine derivative.

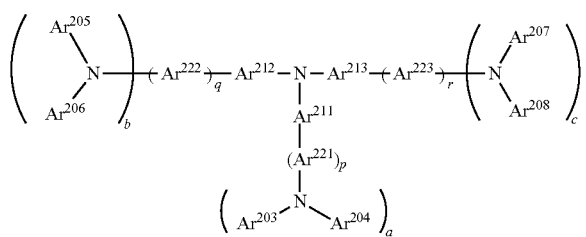

In the above formula, $Ar^{211}$ to $Ar^{213}$ and $Ar^{221}$ to $Ar^{223}$ are each a substituted or unsubstituted arylene group having 6 to 50 ring-forming carbon atoms or a substituted or unsubstituted heteroarylene group having 5 to 50 ring-forming atoms; $Ar^{203}$ to $Ar^{208}$ are each a substituted or unsubstituted aryl group having 6 to 50 ring-forming carbon atoms or a substituted or unsubstituted heteroaryl group having 5 to 50 ring-forming atoms; a to c and p to r are each an integer of 0 to 3; and $Ar^{203}$ and $Ar^{204}$, $Ar^{205}$ and $Ar^{206}$, and $Ar^{207}$ and $Ar^{208}$ may be bonded to each other to form a saturated or unsaturated ring.

Examples of the substituted or unsubstituted aryl group having 6 to 50 ring-forming carbon atoms include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, and 4"-t-butyl-p-terphenyl-4-yl group.

Examples of the substituted or unsubstituted arylene group having 6 to 50 ring-forming carbon atoms include the groups which are derived from the aryl groups mentioned above by removing one hydrogen atom.

Examples of the substituted or unsubstituted heteroaryl group having 5 to 50 ring-forming atoms include 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1, 9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl1-indolyl group, 4-t-butyl1-indolyl group, 2-t-butyl3-indolyl group, and 4-t-butyl3-indolyl group.

Examples of the substituted or unsubstituted heteroarylene group having 6 to 50 ring-forming carbon atoms include the groups which are derived from the heteroaryl groups mentioned above by removing one hydrogen atom.

Further, the hole injecting layer and the hole transporting layer may contain the following compound.

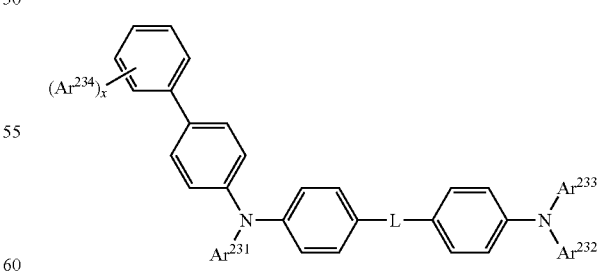

In the above formula, $Ar^{231}$ to $Ar^{234}$ are each a substituted or unsubstituted aryl group having 6 to 50 ring-forming carbon atoms or a substituted or unsubstituted heteroaryl group having 5 to 50 ring-forming atoms; L is a linking group selected from a single bond, a substituted or unsubstituted arylene group having 6 to 50 ring-forming carbon atoms and a substituted or unsubstituted heteroarylene group having 5 to 50 ring-forming atoms; and x is an integer of 0 to 5.

$Ar^{232}$ and $Ar^{233}$ may be bonded to each other to from a saturated or unsaturated ring. Examples of the substituted or unsubstituted aryl group and arylene group each having 6 to 50 ring-forming carbon atoms and the substituted or unsubstituted heteroaryl group and heteroarylene group each having 5 to 50 ring-forming atoms include those mentioned above.

Further examples of the material for the hole injecting layer and the hole transporting layer include a triazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, and an electroconductive oligomer (particularly a thiophene oligomer).

In addition to the above materials, a porphyrin compound, an aromatic tertiary amine compound and a styrylamine compound, particularly the aromatic tertiary amine compound is preferably used as the material for the hole injecting layer and the hole transporting layer.

A compound having two condensed aromatic rings such as 4,4'-bis(N-(1-naphthyl)-N-phenylamino)biphenyl (NPD) and a star-burst compound in which three triphenylamine units are linked such as 4,4',4"-tris(N-(3-methylphenyl)-N-phenylamino)triphenylamine (MTDATA) are also preferred.

In addition, the following nitrogen-containing heterocyclic derivative is usable.

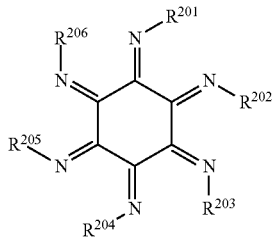

In the above formula, $R^{201}$ to $R^{206}$ are each a substituted or unsubstituted alkyl group having 1 to 50 carbon atoms, a substituted or unsubstituted aryl group having 6 to 50 ring-forming carbon atoms, a substituted or unsubstituted aralkyl group having 7 to 50 carbon atoms, or a substituted or unsubstituted heterocyclic group having 5 to 50 ring-forming atoms; and $R^{201}$ and $R^{202}$, $R^{203}$ and $R^{204}$, $R^{205}$ and $R^{206}$, $R^{201}$ and $R^{206}$, $R^{202}$ and $R^{203}$, and $R^{204}$ and $R^{205}$ may form a condensed ring.

Further, the following compound is usable.

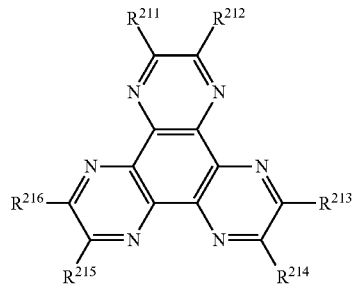

In the above formula, $R^{211}$ to $R^{216}$ are each a substituent group, preferably an electron withdrawing group such as cyano group, nitro group, sulfonyl group, carbonyl group, trifluoromethyl group, and a halogen.

An inorganic compound such as p-type Si and p-type SiC is also usable as the material for the hole injecting layer and the hole transporting layer.

The hole injecting layer and the hole transporting layer are formed by making the above compound into a thin film by a known method such as a vacuum vapor deposition method, a spin coating method, a casting method and LB method. The thickness of the hole injecting layer and the hole transporting layer is not particularly limited and generally 5 nm to 5 μm. Each of the hole injecting layer and the hole transporting layer may be a single layer comprising one or more kinds of the above materials or may be a laminate of two or more hole injecting layers or hole transporting layers each comprising different compounds.

An organic semiconductor layer facilitates the hole injection or the electron injection into the light emitting layer and preferably has an electroconductivity of $10^{-10}$ S/cm or more. The organic semiconductor layer may be formed from an electroconductive oligomer such as a thiophene-containing oligomer and an arylamine-containing oligomer and an electroconductive dendrimer such as an arylamine-containing dendrimer.

The electron blocking layer improves the luminous efficiency by confining the electrons injected from the anode within the light emitting layer. In the organic EL device of the invention, the aromatic tertiary amine compound, etc. for use in the hole transporting layer mentioned above is usable.

The electron injecting layer and the electron transporting layer (electron transporting zone) facilitate the injection of electrons into the light emitting layer and transport the electrons to the light emitting zone, and have a large electron mobility and an electron affinity generally as large as 2.5 eV or more. The electron injecting layer and the electron transporting layer are preferably formed from a material capable of transporting electrons to the light emitting layer at a lower strength of electric field, preferably having an electron mobility of, for example, at least $10^{-6}$ cm$^2$/V·s under an electric field of $10^4$ to $10^6$ V/cm.

When the nitrogen-containing heterocyclic derivative of the invention is used for the electron transporting zone, the electron injecting layer and the electron transporting layer may be formed from the nitrogen-containing heterocyclic derivative alone or in combination with another material.

The material for forming the electron injecting layer and the electron transporting layer in combination with the nitrogen-containing heterocyclic derivative is not particularly limited as long as having the preferred properties mentioned above and may be selected from those commonly used as the electron transporting material in the field of photoconductive materials and those known as the materials for the electron injecting layer and the electron transporting layer of organic EL devices.

The adhesion improving layer is an electron injecting layer comprising a material which is particularly excellent in the adhesion to the cathode. In the organic EL device of the invention, the compound of the invention is preferably used in the electron injecting layer, the electron transporting layer, and the adhesion improving layer In a preferred embodiment of the organic EL device of the invention, the device contains a reducing dopant in the electron transporting region or in the interfacial region between the cathode and the organic layer. In the present invention, an organic EL device containing the compound of the invention and a reducing dopant is preferred. The reducing dopant is a compound capable of reducing the electron transporting compound. Various compounds having a certain degree of reducing power are usable as the reducing dopant. For example, at least one substance selected from the group consisting of an alkali metal, an alkaline earth metal, a rare earth metal, an alkali metal oxide, an alkali metal halide, an alkaline earth metal oxide, an alkaline earth metal halide, a rare earth metal oxide, a rare earth metal halide, an organic complex of alkali metal, an organic complex of alkaline earth metal, and an organic complex of rare earth metal may be advantageously used.

Preferred reducing dopants are those having a work function of 2.9 eV or less such as at least one alkali metal selected from the group consisting of Na (work function: 2.36 eV), K (work function: 2.28 eV), Rb (work function: 2.16 eV) and Cs (work function: 1.95 eV) and at least one alkaline earth metal selected from the group consisting of Ca (work function: 2.9 eV), Sr (work function: 2.0 to 2.5 eV) and Ba (work function: 2.52 eV). More preferred are at least one alkali metal selected from the group consisting of K, Rb and Cs, still more preferred are Rb or Cs, and most preferred is Cs. These alkali metals have an extremely high reducing power and improve the luminance and the life of organic EL device when added to the electron injecting zone in a small amount. As the reducing dopant having a work function of 2.9 eV or less, a combination of two or more alkali metals is preferable and a combination containing Cs such as Cs with Na, Cs with K, Cs with Rb, and Cs with Na and K is particularly preferred. Since the reducing power is efficiently exhibited by the inclusion of Cs in the combination, the luminance and the life of organic EL device are improved by adding such a combination to the electron injecting zone.

In the present invention, an electron injecting layer which is constituted of an insulating material or a semiconductor may be disposed between the cathode and the organic layer. By such an electron injecting layer, the leak of electric current is effectively prevented to improve the electron injecting ability. Preferred examples of the insulating material include at least one metal compound selected from the group consisting of an alkali metal chalcogenide, an alkaline earth metal chalcogenide, an alkali metal halide, and an alkaline earth metal halide. An electron injecting layer constituted of the above alkali metal chalcogenide is preferred because the electron injecting property is further improved. Preferred alkali metal chalcogenides include $Li_2O$, $K_2O$, $Na_2S$, $Na_2Se$, and $Na_2O$; preferred alkaline earth metal chalcogenides include CaO, BaO, SrO, BeO, BaS, and CaSe; preferred alkali metal halides include LiF, NaF, KF, LiCl, KCl, and NaCl; and preferred alkaline earth metal halides include fluoride such as $CaF_2$, $BaF_2$, $SrF_2$, $MgF_2$, and $BeF_2$ and halide other than fluoride.

Examples of the semiconductor constituting the electron transporting layer include an oxide, a nitride and an oxynitride of at least one element selected from Ba, Ca, Sr, Yb, Al, Ga, In, Li, Na, Cd, Mg, Si, Ta, Sb, and Zn, which are used singly or in combination of two or more. It is preferred that the inorganic compound constituting the electron transporting layer forms a fine crystalline or amorphous insulating thin film. When constituted of the insulating thin film described above, the electron injecting layer is made more uniform to reduce the pixel defect such as dark spots. Examples of such a inorganic compound include the alkali metal chalcogenide, the alkaline earth metal chalcogenide, the alkali metal halide and the alkaline earth metal halide which are described above.

The cathode injects electrons into the electron injecting layer, the electron transporting layer or the light emitting layer, and therefore, is formed from an electrode material such as a metal, an alloy, an electroconductive compound, or a mixture thereof, which has a small work function (4 eV or less). Examples of the electrode material include sodium, sodium-potassium alloy, magnesium, lithium, magnesium-silver alloy, aluminum-aluminum oxide, aluminum-lithium alloy, indium, and rare earth metal.

The cathode is formed by making the electrode material into a thin film by a method such as a vapor deposition method and a sputtering method.

When the light emitted from the light emitting layer is allowed to pass through the cathode, the transmittance of the cathode to the emitted light is preferably larger than 10%.

The sheet resistance of the cathode is preferably several hundreds Ω/□ or less, and the thickness of the cathode is generally 10 nm to 1 μm, preferably 50 to 200 nm.

Since an electric field is applied to ultra-thin films of organic EL device, pixel defects are likely to occur due to leak of current and short circuit. To prevent the defects, an insulating thin film is preferably inserted between a pair of electrodes. Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture thereof and a laminate of layers each containing the above material are usable.

By the above method using the materials mentioned above, the organic EL device is produced by forming an anode, a light emitting layer, an optional hole injecting layer or hole transporting layer, an optional electron injecting layer or an electron transporting layer, and a cathode. Alternatively, the organic EL device is produced by forming the layers in reverse order from the cathode to the anode.

The production of the organic EL device will be described below with reference to an organic EL device having a construction in which an anode, a hole injecting layer, a light emitting layer, an electron injecting layer and a cathode are formed successively on a light-transmissive substrate.

First, an anode is formed on a suitable light-transmissive substrate by making an anode material into a thin film of 1 μm or thick, preferably 10 to 200 nm thick by a method such as a vapor deposition method or a sputtering method. Then, a hole injecting layer is formed on the anode. The hole injecting layer is formed by a method such as a vacuum vapor deposition method, a spin coating method, a casting method and LB method each mentioned above, and preferably by the vacuum vapor deposition method because a uniform film is easily obtained and pin holes hardly occur. The vapor deposition conditions for forming the hole injecting layer vary depending upon the compound (material for the hole injecting layer) to be used and the intended crystal structure and recombination structure of the hole injecting layer, and are preferably selected from a deposition source temperature of 50 to 450° C., a vacuum degree of $10^{-7}$ to $10^{-3}$ Torr, a deposition speed of 0.01 to 50 nm/s, a substrate temperature of −50 to 300° C., and a film thickness of 5 nm to 5 μm.

Next, a light emitting layer is formed on the hole injecting layer. The light emitting layer is formed by making a desired organic light emitting material into a thin film by a method such as a vacuum vapor deposition method, a sputtering method, a spin coating method, and a casting method, preferably by the vacuum vapor deposition method because a uniform film is easily obtained and pin holes hardly occur. The vapor deposition conditions for forming the light emitting layer vary depending upon the compound to be used and are generally selected from the conditions described with respect to the hole injecting layer.

Next, an electron injecting layer is formed on the light emitting layer. Like the formation of the hole injecting layer and the light emitting layer, the electron injecting layer is preferably formed by the vacuum vapor deposition method because a uniform film is required. The vapor deposition conditions thereof are selected from those described with respect to the hole injecting layer and the light emitting layer.

Although depending upon that the nitrogen-containing heterocyclic derivative of the invention is included in which layer of the light emitting zone and the hole transporting zone, the derivative may be co-deposited with another material by the vacuum vapor deposition method. In the spin coating method, the derivative may be mixed with another material.

Finally, by laminating a cathode, the organic EL device is obtained.

The cathode is made of a metal and is formed by the vacuum vapor method or the sputtering method, with the vacuum vapor method being preferred because the underlying organic layer is prevented from being damaged during the film formation.

In the production of the organic EL device, the layers from the anode to the cathode are preferably formed successively and continuously by a single evacuation operation.

Each layer of the organic EL device of the invention may be formed by any one of known methods such as a vacuum vapor deposition method and a spin coating method, although not particularly limited. The organic thin-film layer containing the compound of formula (1) in the organic EL device is formed by a known method such as a vacuum vapor deposition method, a molecular beam epitaxy method (MBE method) and a coating method, for example, a dipping method, a spin coating method, a casting method, a bar coating method and a roll coating method each using a solution of the compound in a solvent.

The thickness of each organic thin film layer in the organic EL device of the invention is not particularly limited and preferably several nanometers to 1 μm because an excessively small thickness may cause defects such as pin holes and an excessively large thickness may require a high driving voltage.

When a direct voltage of 5 to 40 V is applied to the organic EL device so that the anode has a polarity of + and the cathode has a polarity of −, the emission of light is observed. When a voltage is applied in a reverse polarity, no electric current flows and no light is emitted. When an alternating voltage is applied, a uniform light emission is observed only when the anode has a polarity of + and the cathode has a polarity of −. The waveform of the alternating voltage to be applied is not particularly limited.

EXAMPLES

The present invention will be described in more detail with reference to the examples. However, it should be noted that the scope of the invention is not limited thereto.

Synthesis Example 1 (Synthesis of Compound 1)

Compound 1

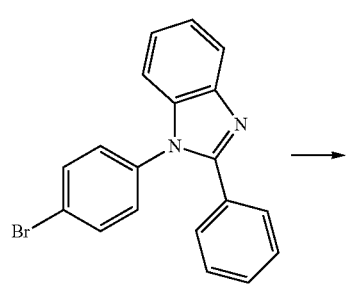

-continued

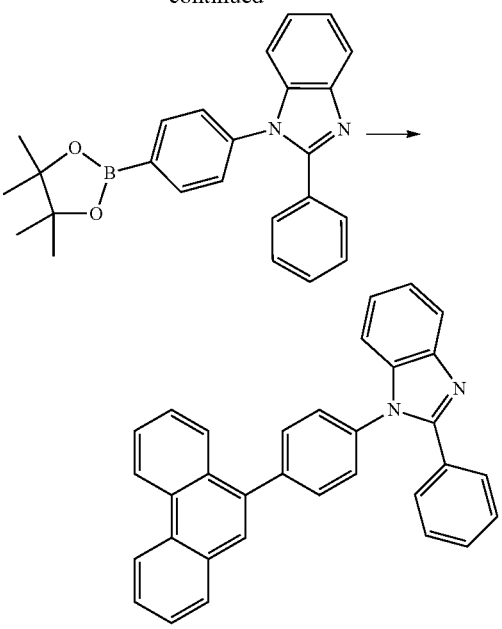

Into a 100-mL three-necked flask, 3.0 g (8.6 mmol) of 1-(4-bromophenyl)-2-phenyl-1H-benzimidazole, 2.2 g (8.7 mmol) of bis(pinacolato)diboronic acid, 0.21 g (0.29 mmol) of [1,1'-bis(diphenylphosphino)ferrocene] dichloropalladium (II), 2.5 g (25 mmol) of potassium acetate, and 50 ml of DMF were charged and the mixture was heated at 80° C. for 3 h in argon flow. After confirming the disappearance of the starting boron compound, the mixture was cooled to room temperature. After adding 2.2 g (8.6 mmol) of 9-bromophenanthrene, 0.21 g (0.29 mmol) of [1,1'-bis(diphenylphosphino)ferrocene] dichloropalladium (II), and 21 mL of a 2 M aqueous solution of sodium carbonate, the mixture was further heated at 80° C. for 3 h under stirring. After the reaction, water was added. The precipitated crystals were corrected by filtration, washed with water and methanol, and dried under reduced pressure, to obtain a crude reaction product, which was then purified by a column chromatography (silica gel, dichloromethane: hexane), to obtain 2.5 g of white crystals. The obtained crystals were identified to Compound 1 by FD-MS (field desorption mass spectrometry). Yield: 65%.

Synthesis Example 2 (Synthesis of Compound 2)

Compound 2

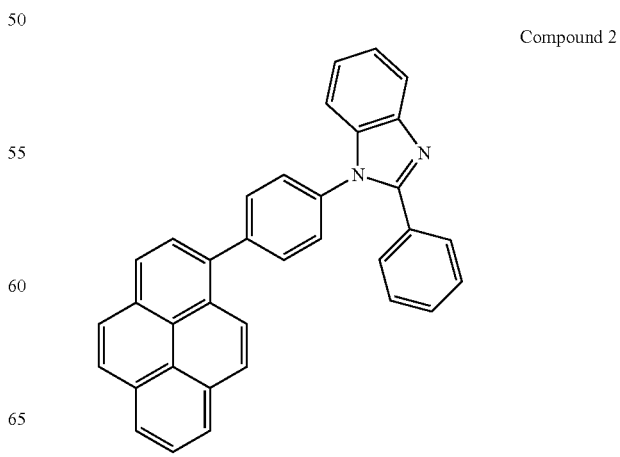

Compound 2 was obtained in the same manner as in Synthesis Example 1 except for using 9-bromopyrene in place of 9-bromophenanthrene. Yield: 50%.

Synthesis Example 3 (Synthesis of Compound 3)

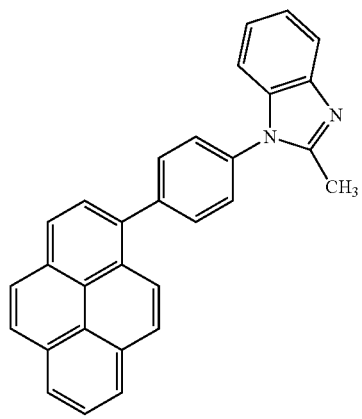 [SMILES: Cc1nc2ccccc2n1-c1ccc(-c2ccc3ccc4cccc5ccc2c3c45)cc1]

Compound 3 was obtained in the same manner as in Synthesis Example 1 except for using 1-(4-bromophenyl)-2-methyl-1H-benzimidazole in place of 1-(4-bromophenyl)-2-phenyl-1H-benzimidazole and using 9-bromopyrene in place of 9-bromophenanthrene. Yield: 55%.

Synthesis Example 4 (Synthesis of Compound 4)

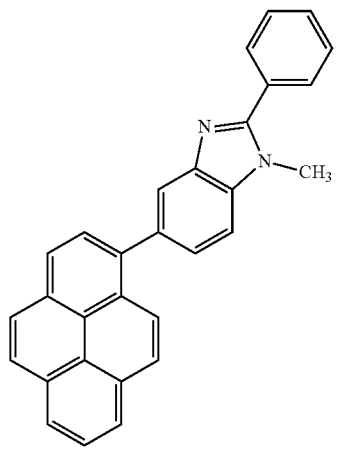 [SMILES: Cn1c(-c2ccccc2)nc2cc(-c3ccc4ccc5cccc6ccc3c4c56)ccc21]

Compound 4 was obtained in the same manner as in Synthesis Example 1 except for using 5-bromo-1-methyl-2-phenyl-1H-benzimidazole in place of 1-(4-bromophenyl)-2-phenyl-1H-benzimidazole and using 9-bromopyrene in place of 9-bromophenanthrene. Yield: 40%.

Synthesis Example 5 (Synthesis of Compound 5)

(5-1) Synthesis of Intermediate A1

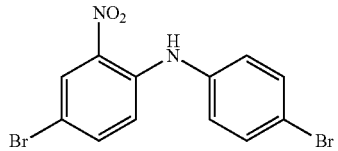 [SMILES: O=[N+]([O-])c1cc(Br)ccc1Nc1ccc(Br)cc1]

A mixture of 40 g (0.14 mol) of 2,5-dibromonitrobenzene, 48 g (0.58 mol) of sodium acetate, and 26 g (0.15 mol) of 4-bromoaniline was heated at 120° C. for 8 h under stirring, dissolved in 500 mL of dichloromethane, and successively washed with water and a saturated saline solution. After drying over anhydrous sodium sulfate, the solvent was evaporated off under reduced pressure. The crystals purified by a silica gel column chromatography (eluent: dichloromethane) was washed with methanol to obtain 20 g of Intermediate A1. Yield: 38%.

(5-2) Synthesis of Intermediate A2

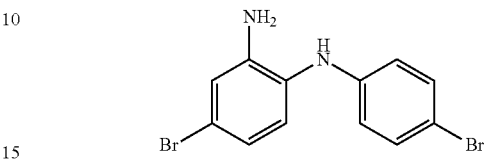

To a solution of 20 g (54 mmol) of Intermediate A1 in 200 mL tetrahydrofuran, a solution of 48 g (0.28 mol) of sodium hydrosulfite in 200 mL of water was added dropwise in argon atmosphere at room temperature under stirring. After adding 10 mL of methanol, the stirring was continued for 5 h. After the reaction solution turned transparent to show the completion of the reaction, 200 mL of ethyl acetate was added and the solution was neutralized by a sodium hydrogencarbonate aqueous solution. The organic layer separated was washed with a saturated saline solution and dried over anhydrous magnesium sulfate. Then, the solvent was evaporated off under reduced pressure to obtain 18 g of Intermediate A2. Yield: 100%.

(5-3) Synthesis of Intermediate A3

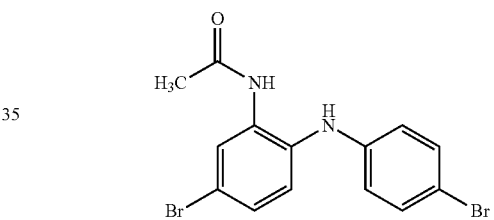

To a solution of 5.0 g Intermediate A2 (15 mmol) in 50 mL of N-methylpyrrolidone, 2.2 g (22 mmol) of acetic anhydride was added dropwise and the mixture was stirred for 3 h at room temperature. After the reaction, the reaction mixture was poured into 200 mL of water. The precipitated solid was separated by filtration and dried under reduced pressure to obtain 4.9 g of Intermediate A3. Yield: 88%

(5-4) Synthesis of Intermediate A4

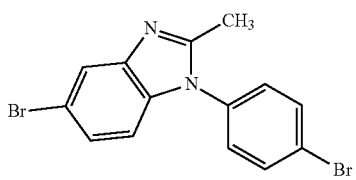 [SMILES: Cc1nc2cc(Br)ccc2n1-c1ccc(Br)cc1]

To a solution of 4.9 g (13 mmol) of Intermediate A3 in 50 mL of xylene, 0.25 g (1.3 mmol) of p-toluenesulfonic acid monohydrate was added. The resulting solution was refluxed under nitrogen atmosphere for 8 h under heating to azeotropically remove water. The reaction solution was cooled to room temperature and purified by a silica gel column chromatography (eluent: dichloromethane). The obtained crystals were washed with methanol to obtain 3.0 g of Intermediate A4. Yield: 64%.

(5-5) Synthesis of Compound 5

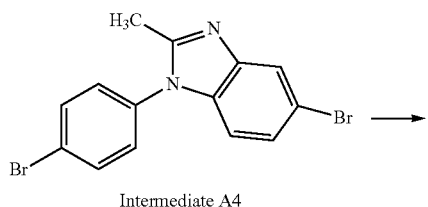

Intermediate A4

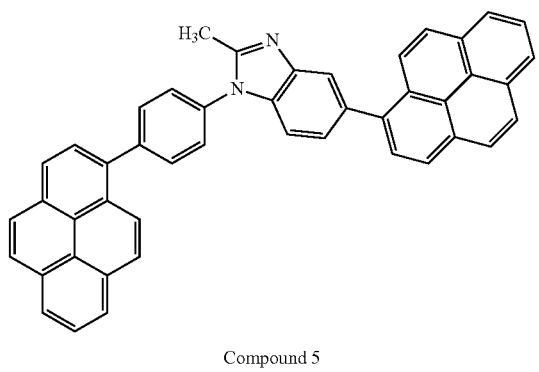

Compound 5

Into a 300-mL three-necked flask, 3.0 g (8.2 mmol) of Intermediate A4, 4.4 g (18 mmol) of pyrene-1-boronic acid, 0.38 g (0.33 mmol) of tetrakistriphenylphosphine palladium (0), 60 mL of toluene, 30 mL of 1,2-dimethoxyethane, and 27 mL of a 2 M sodium carbonate aqueous solution were charged and the mixture was refluxed for 8 h under heating in argon flow. After the reaction, water was added. The precipitated solid was washed with water and further with methanol. The obtained crude crystals were washed with 50 mL of 1,2-dimethoxyethane twice and with 50 mL of toluene twice, to obtain 3.5 g of a pale yellow powder, which was identified to Compound 5 by FD-MS (field desorption mass spectrometry) Yield: 70%.

Synthesis Example 6 (Synthesis of Compound 6)

(6-1) Synthesis of Intermediate A5

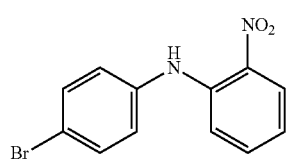

Intermediate A5

A mixture of 39 g (0.27 mol) of 2-fluoronitrobenzene, 90 g (1.1 mol) of sodium acetate, and 47 g (0.27 mol) of 4-bromoaniline was heated at 120° C. for 8 h under stirring and dissolved in 300 mL of dichloromethane. The resulting solution was successively washed with water and a saturated saline solution and dried over anhydrous sodium sulfate, and then, the solvent was evaporated off under reduced pressure. After purifying by a silica gel column chromatography (eluent: dichloromethane), the obtained crystals were washed with methanol to obtain 41 g of Intermediate A5. Yield: 50%

(6-2) Synthesis of Intermediate A6

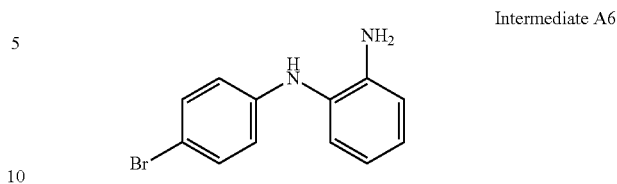

Intermediate A6

To a solution of 15 g (51 mmol) of Intermediate A5 in 150 mL of tetrahydrofuran, a solution of 45 g (0.26 mol) sodium hydrosulfite in 150 mL of water was added dropwise in argon atmosphere at room temperature under stirring and 10 mL of methanol was further added to continue the stirring for 3 h. After the reaction solution turned transparent to show the completion of the reaction, 200 mL of ethyl acetate was added and the solution was neutralized by a sodium hydrogencarbonate aqueous solution. The organic layer separated was washed with a saturated saline solution and dried over anhydrous magnesium sulfate, and then, the solvent was evaporated off under reduced pressure to obtain 13.5 g of Intermediate A6. Yield: 100%.

(6-3) Synthesis of Intermediate A7

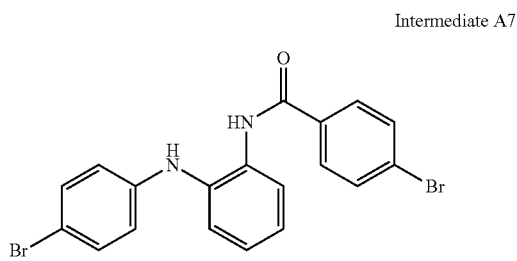 [SMILES: O=C(Nc1ccccc1Nc1ccc(Br)cc1)c1ccc(Br)cc1]

Intermediate A7

A solution of 10 g (38 mmol) of Intermediate A6 in 100 mL of N-methylpyrrolidone was added dropwise with 10 g (46 mmol) of 4-bromobenzoyl chloride and stirred for 3 h at room temperature. After the reaction, the reaction mixture was poured into 500 mL of water. The precipitated solid was separated by filtration and dried under reduced pressure, to obtain 13.6 g of Intermediate A7. Yield: 80%.

(6-4) Synthesis of Intermediate A8

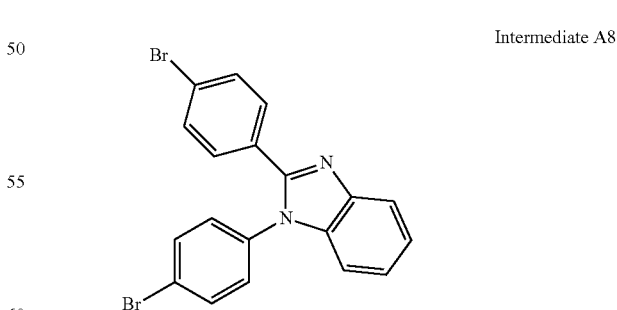

Intermediate A8

A solution of 13.6 g (30 mmol) of Intermediate A7 in 100 mL of xylene was added with 0.6 g (3.2 mmol) of p-toluenesulfonic acid monohydrate and refluxed under nitrogen atmosphere for 8 h under heating to azeotropically remove water. The reaction solution was cooled to room temperature and purified by a silica gel column chromatography (eluent:

dichloromethane). The obtained crystals were washed with methanol to obtain 7.8 g of Intermediate A8. Yield: 60%.

(6-5) Synthesis of Compound 6

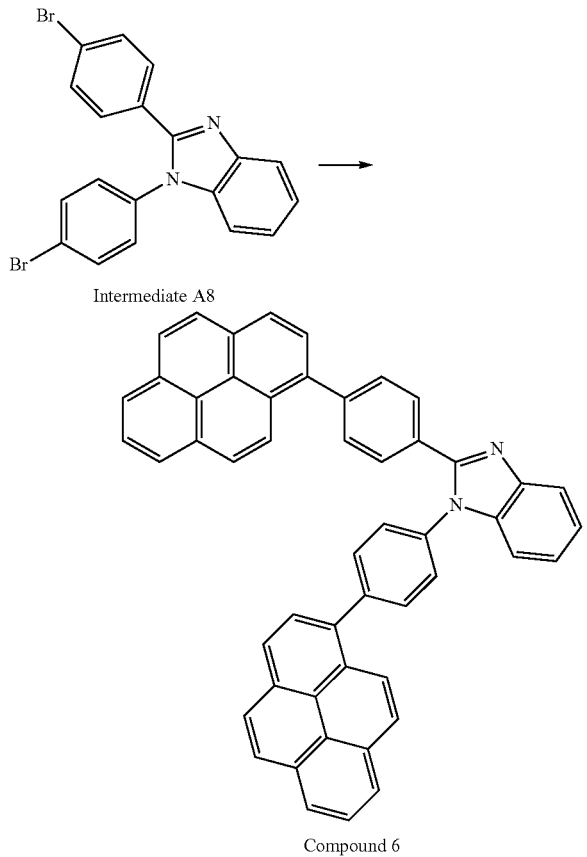

Into a 500-mL three-necked flask, 7.8 g (18 mmol) of Intermediate A8, 9.9 g (40 mmol) of pyrene-1-boronic acid, 0.83 g (0.72 mmol) of tetrakistriphenylphosphine palladium (0), 120 mL of toluene, 60 mL of 1,2-dimethoxyethane, and 60 mL of a 2 M sodium carbonate aqueous solution were charged and the mixture was refluxed for 8 h under heating in argon flow. After the reaction, water was added. The precipitated solid was washed with water and further with methanol. The obtained crude crystals were washed with 100 mL of 1,2-dimethoxyethane twice and with 100 mL of toluene twice, to obtain 9.1 g of pale yellow powder, which was identified to Compound 6 by FD-MS (field desorption mass spectrometry). Yield: 74%.

Synthesis Example 7 (Synthesis of Compound 7)

(7-1) Synthesis of Intermediate B1

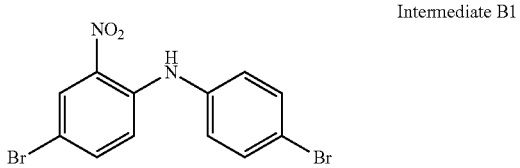 [SMILES: Nc1cc(Br)ccc1Nc1ccc(Br)cc1]

A mixture of 40 g (0.14 mol) of 2,5-dibromonitrobenzene, 48 g (0.58 mol) of sodium acetate, and 26 g (0.15 mol) of 4-bromoaniline was heated at 120° C. for 8 h under stirring, dissolved in 500 mL of dichloromethane, and successively washed with water and a saturated saline solution. After drying over anhydrous sodium sulfate, the solvent was evaporated off under reduced pressure and the residue was purified by a silica gel column chromatography (eluent: dichloromethane). The obtained crystals were washed with methanol to obtain 20 g of Intermediate B1. Yield: 38%.

(7-2) Synthesis of Intermediate B2

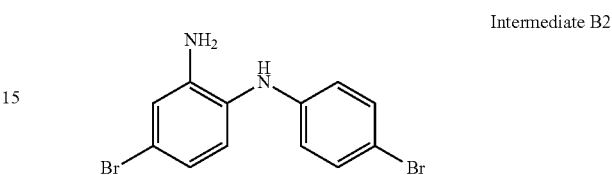

To a solution of 20 g (54 mmol) of Intermediate B1 in 200 mL of tetrahydrofuran, a solution of 48 g (0.28 mol) of sodium hydrosulfite in 200 mL of water was added dropwise in argon atmosphere at room temperature under stirring. After adding 10 mL of methanol, the stirring was continued for 5 h. After the solution turned to transparent to show the completion of the reaction, the reaction solution was added with 200 mL of ethyl acetate and neutralized by a sodium hydrogencarbonate aqueous solution. The organic layer separated was washed with a saturated saline solution and dried over anhydrous magnesium sulfate. Then, the solvent was evaporated off under reduced pressure to obtain 18 g of Intermediate B2. Yield: 100%.

(7-3) Synthesis of Intermediate B3

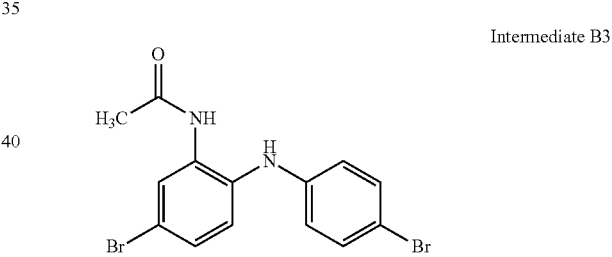

A solution of 5.0 g (15 mmol) of Intermediate B2 in 50 mL of N-methylpyrrolidone was added dropwise with 2.2 g (22 mmol) of acetic anhydride and stirred at room temperature for 3 h. After the reaction, the reaction mixture was poured into 200 mL of water. The precipitated solid was separated by filtration and dried under reduced pressure, to obtain 4.9 g of Intermediate B3. Yield: 88%.

(7-4) Synthesis of Intermediate B4

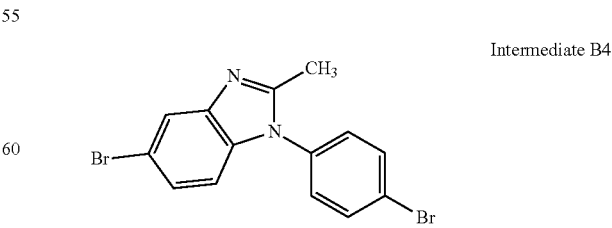

A solution of 4.9 g (13 mmol) of Intermediate B3 in 50 mL of xylene was added with 0.25 g (1.3 mmol) of p-toluenesulfonic acid monohydrate and refluxed in nitrogen atmosphere for 8 h under heating to azeotropically remove water. The reaction solution was cooled to room temperature and purified by a silica gel column chromatography (eluent: dichloromethane) to obtain 3.0 g of Intermediate B4. Yield: 64%.

(7-5) Synthesis of Compound 7

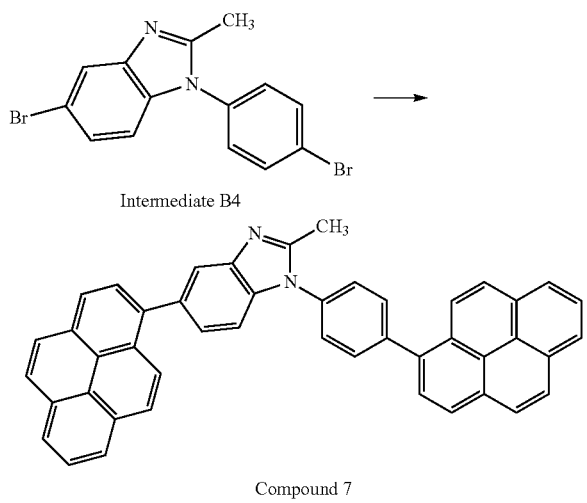

Intermediate B4

Compound 7

Into a 500-mL three-necked flask, 3.0 g (8.2 mmol) of Intermediate B4, 4.4 g (18 mmol) of pyrene-1-boronic acid, 0.38 g (0.33 mmol) of tetrakistriphenylphosphine palladium (0), 80 mL of toluene, 40 mL of 1,2-dimethoxyethane, and 27 mL of a 2 M sodium carbonate aqueous solution were charged and the mixture was refluxed in argon flow for 8 h under heating. After the reaction, water was added. The precipitated sold was washed with water and further with methanol. The obtained crude crystals were washed with 100 mL of 1,2-dimethoxyethane twice and 100 mL of toluene twice, to obtain 3.5 g of pale yellow powder, which was identified to Compound 7 by FD-MS (field desorption mass spectrometry). Yield: 70%.

Synthesis Example 8 (Synthesis of Compound 8)

(8-1) Synthesis of Intermediate C1

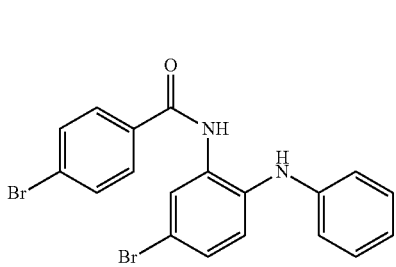

Intermediate C1

A solution of 5.0 g (19 mmol) of 4-bromo-N-1-phenyl-o-phenylenediamine in 50 mL of N-methylpyrrolidone was added dropwise with 5.0 g (23 mmol) of 4-bromobenzoyl chloride and stirred at room temperature for 2 h. After the reaction, the reaction mixture was poured into 200 mL of water. The precipitated sold was separated by filtration and dried under reduced pressure, to obtain 7.0 g of Intermediate C1. Yield: 83%.

(8-2) Synthesis of Intermediate C2

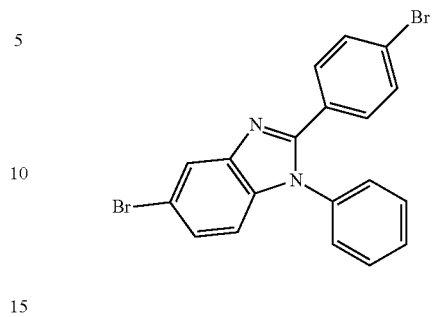

Intermediate C2

A solution of 7.0 g (16 mmol) of Intermediate C1 in 70 mL of xylene was added with 0.30 g (1.6 mmol) of p-toluene-sulfonic acid monohydrate and refluxed in nitrogen atmosphere for 8 h under heating to azeotropically remove water. The reaction solution was cooled to room temperature and purified by a silica gel column chromatography (eluent: dichloromethane), to obtain 4.7 g of Intermediate C2. Yield: 70%.

(8-3) Synthesis of Compound 8

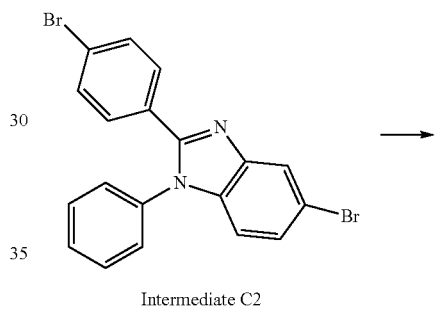

Intermediate C2

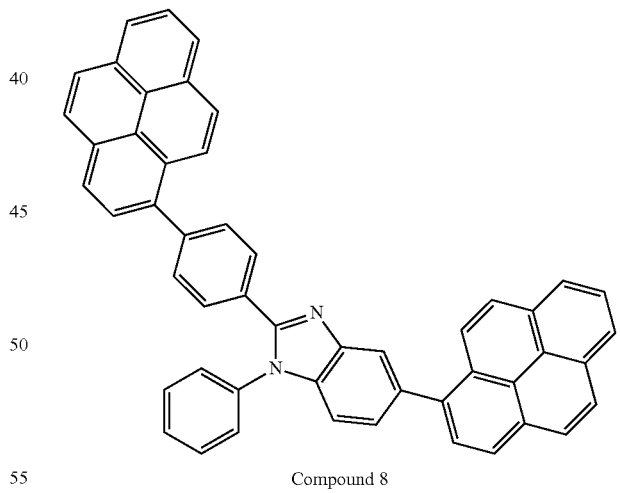

Compound 8

Into a 500-mL three-necked flask, 4.7 g (11 mmol) of Intermediate C2, 5.9 g (24 mmol) of pyrene-1-boronic acid, 0.51 g (0.44 mmol) of tetrakistriphenylphosphine palladium (0), 80 mL of toluene, 40 mL of 1,2-dimethoxyethane, and 33 mL of a 2 M sodium carbonate aqueous solution were charged and the mixture was refluxed in argon flow for 8 h under heating. After the reaction, water was added. The precipitated solid was washed with water and further with methanol. The obtained crude crystals were washed with 50 mL of 1,2-dimethoxyethane twice and 50 mL of toluene twice, to obtain 4.4 g of pale yellow powder, which was identified to Compound 8 by FD-MS (field desorption mass spectrometry). Yield: 60%.

Synthesis Example 9 (Synthesis of Compound 9)

(9-1) Synthesis of Intermediate D1

Intermediate D1

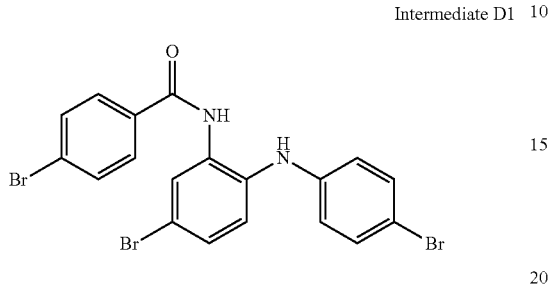

A solution of 5.0 g (15 mmol) of Intermediate B2 in 50 mL of N-methylpyrrolidone was added dropwise with 3.8 g (17 mmol) of 4-bromobenzoyl chloride and stirred at room temperature for 2 h. After the reaction, the reaction mixture was poured into 200 mL of water. The precipitated sold was separated by filtration and dried under reduced pressure, to obtain 7.0 g of Intermediate D1. Yield: 91%.

(9-2) Synthesis of Intermediate D2

Intermediate D2

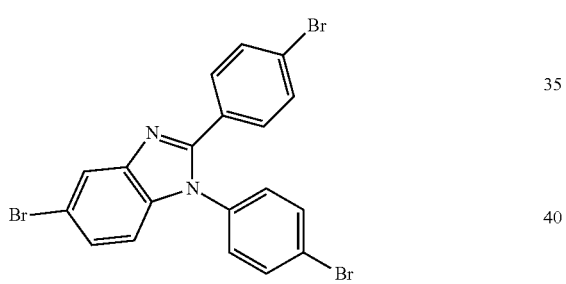

A solution of 7.0 g (13 mmol) of Intermediate D1 in 50 mL of xylene was added with 0.25 g (1.3 mmol) of p-toluenesulfonic acid monohydrate and reflux under nitrogen atmosphere for 8 h under heating to azeotropically remove water. The reaction solution was cooled to room temperature and purified by a silica gel column chromatography (eluent: dichloromethane), to obtain 3.4 g of Intermediate D2. Yield: 50%.

(9-3) Synthesis of Compound 9

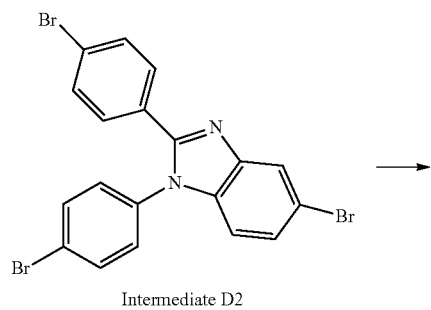

Intermediate D2

→

-continued

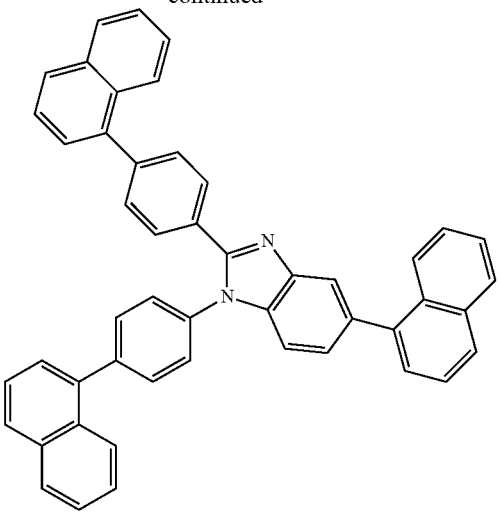

Compound 9

Into a 300-mL three-necked flask, 3.4 g (6.7 mmol) of Intermediate D2, 3.8 g (22 mmol) of naphthalene-1-boronic acid, 0.47 g (0.41 mmol) of tetrakistriphenylphosphine palladium (0), 60 mL of toluene, 30 mL of 1,2-dimethoxyethane, and 30 mL of a 2 M sodium carbonate aqueous solution were charged and the mixture was refluxed in argon flow for 8 h under heating. After the reaction, water was added. The precipitated solid was washed with water and further with methanol. The obtained crude crystals were washed with 50 mL of 1,2-dimethoxyethane twice and 50 mL of toluene twice, to obtain 2.5 g of pale yellow powder, which was identified to Compound 9 by FD-MS (field desorption mass spectrometry). Yield: 57%.

Example 1

Production of Organic EL Device Having an Electron Injecting Layer Containing the Compound of the Invention A glass substrate (product of Geomatec Company) of 25 mm×75 mm×1.1 mm thickness having an ITO transparent electrode (anode) was ultrasonic-cleaned in isopropyl alcohol for 5 min and then UV ozone-cleaned for 30 min. The cleaned glass substrate was mounted to a substrate holder of a vacuum vapor deposition apparatus. First, a film of N,N'-bis(N,N'-diphenyl-4-aminophenyl)-N,N-diphenyl-4,4'-diamino-1,1'-biphenyl (TPD232 film) was formed in a thickness of 60 nm so as to cover the transparent electrode. TPD232 film worked as an hole injecting layer. Successively, a film of 4,4'-bis[N-(1-naphthyl)-N-phenylamino]biphenyl (NPD film) was formed on TPD232 film in a thickness of 20 nm. NPD film worked as a hole transporting layer.

Further, on NPD film the following styryl derivative (DPVDPAN) and the following styrylamine derivative (S1) were deposited into a thin film of 40 nm thick in a thickness ratio of 40:2, to form a blue light emitting layer.

DPVDPAN

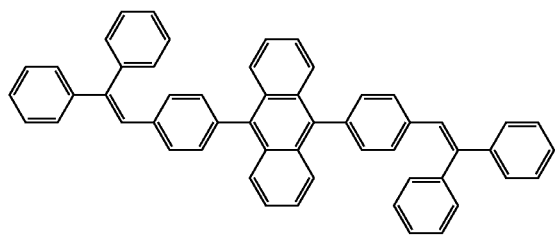

S1

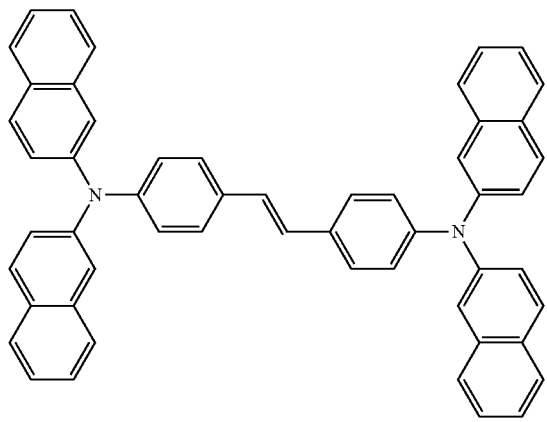

On the film, Compound 1 was vapor-deposited into a thin film in a thickness of 20 nm to form an electron transporting layer. Thereafter, LiF film was formed in a thickness of 1 nm. On LiF film, metallic Al was vapor-deposited in a thickness of 150 nm to form a metal cathode, thereby producing an organic EL device.

Examples 2-8

Each organic EL device was produced in the same manner as in Example 1 except for using Compound 2, 4, 5, 6, 7, 8, or 9 in place of Compound 1.

Comparative Example 1

An organic EL device was produced in the same manner as in Example 1 except for using the following Compound A described in WO 2004/080975 A1 in place of Compound 1.

Compound A

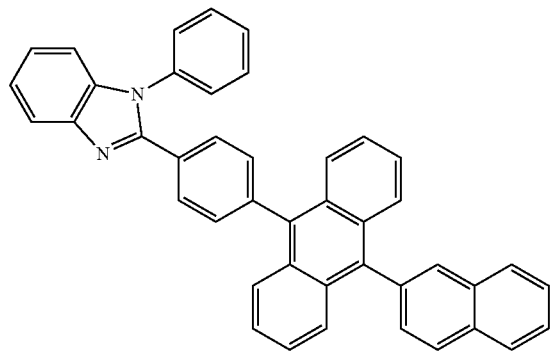

Comparative Example 2

An organic EL device was produced in the same manner as in Example 1 except for using the following Compound B described in JP 2002-38141A in place of Compound 1.

Compound B

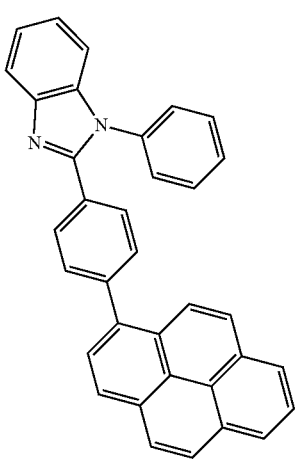

Comparative Example 3

An organic EL device was produced in the same manner as in Example 1 except for using Alq (aluminum complex of 8-hydroxyquinoline) in place of Compound 1.

Evaluation of Organic EL Devices

The organic EL devices obtained in Examples 1-8 and Comparative Examples 1-3 were measured for the luminance, luminous efficiency and chromaticity at direct current driving voltages shown in Table 1, and the emission color was observed.

TABLE 1

|  | Compound of electron injecting layer | Voltage (V) | Current density (mA/cm$^2$) |
|---|---|---|---|
| Examples | | | |
| 1 | Compound 1 | 4.5 | 10.0 |
| 2 | Compound 2 | 4.6 | 10.0 |
| 3 | Compound 4 | 4.5 | 10.0 |
| 4 | Compound 5 | 4.8 | 10.0 |
| 5 | Compound 6 | 4.7 | 10.0 |
| 6 | Compound 7 | 4.6 | 10.0 |
| 7 | Compound 8 | 4.8 | 10.0 |
| 8 | Compound 9 | 4.6 | 10.0 |
| Comparative Examples | | | |
| 1 | Compound A | 6.1 | 10.0 |
| 2 | Compound B | 5.6 | 10.0 |
| 3 | Alq | 6.2 | 10.0 |

|  | Luminance (cd/m$^2$) | Luminous efficiency (cd/A) | Emission color |
|---|---|---|---|
| Examples | | | |
| 1 | 823.7 | 8.24 | blue |
| 2 | 810.5 | 8.11 | blue |
| 3 | 829.2 | 8.29 | blue |
| 4 | 814.4 | 8.14 | blue |
| 5 | 785.9 | 7.86 | blue |
| 6 | 821.4 | 8.21 | blue |

TABLE 1-continued

| 7 | 798.3 | 7.98 | blue |
|---|---|---|---|
| 8 | 807.5 | 8.08 | blue |
| Comparative Examples | | | |
| 1 | 622.9 | 6.23 | blue |
| 2 | 612.1 | 6.12 | blue |
| 3 | 480.3 | 4.80 | blue |

As seen from Table 1, a device exhibiting an extremely high luminance and luminous efficiency is obtained by using the nitrogen-containing heterocyclic derivative of the invention in the electron injecting layer.

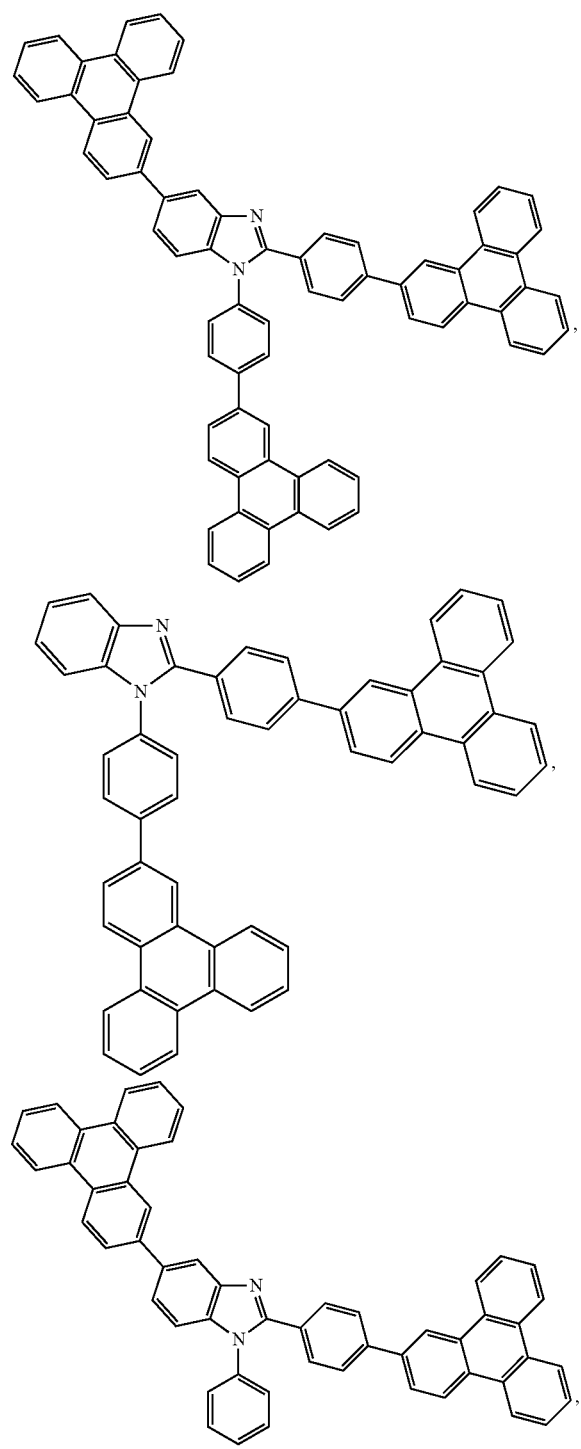
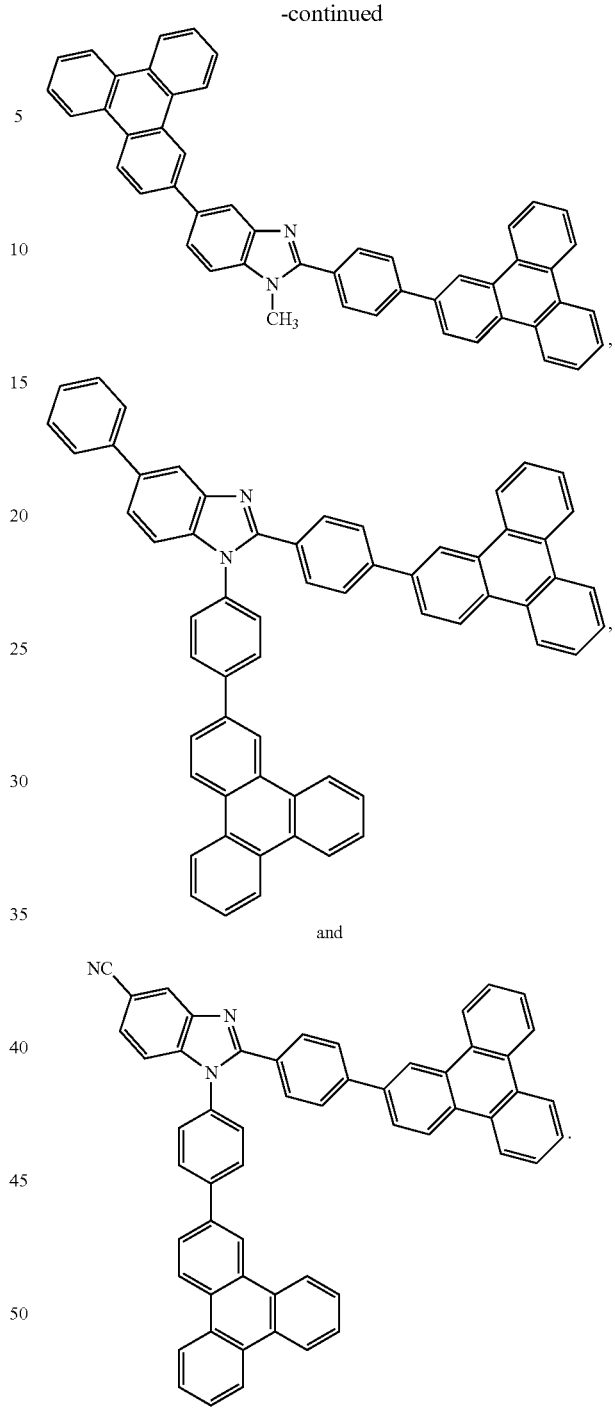

The invention claimed is:

1. An organic electroluminescence device comprising an organic thin-film layer which is disposed between a cathode and an anode and comprises one or more layers having a light emitting layer, wherein at least one layer of the organic thin-film layer comprises a nitrogen-comprising heterocyclic derivative represented by formula (1):

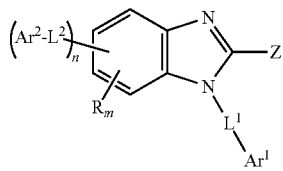

(1)

wherein
R is hydrogen atom, a substituted or unsubstituted alkyl group having 1 to 50 carbon atoms, a substituted or unsubstituted cycloalkyl group having 3 to 50 ring-forming carbon atoms, a substituted or unsubstituted haloalkyl group having 1 to 50 carbon atoms, a substituted or unsubstituted aryl group having 6 to 20 ring-forming carbon atoms, a substituted or unsubstituted heteroaryl group having 5 to 20 ring-forming atoms, halogen atom, cyano group, or nitro group;

m is an integer of 0 to 4, and, when m is an integer of 2 to 4, R groups may be the same or different and an adjacent pair of R groups may be bonded to each other to form a substituted or unsubstituted, saturated or unsaturated linking group which completes a ring structure;

$L^1$ and $L^2$ are each independently a single bond, a substituted or unsubstituted arylene group having 6 to 20 ring-forming carbon atoms, or a substituted or unsubstituted heteroarylene group having 5 to 20 ring-forming atoms, with the proviso that a substituted or unsubstituted anthracenylene group and a substituted or unsubstituted fluorenylene group are excluded;

$Ar^1$ is hydrogen atom, a substituted or unsubstituted alkyl group having 1 to 50 carbon atoms, a substituted or unsubstituted cycloalkyl group having 3 to 50 ring-forming carbon atoms, a substituted or unsubstituted haloalkyl group having 1 to 50 carbon atoms, a substituted or unsubstituted aryl group having 6 to 20 ring-forming carbon atoms, or a substituted or unsubstituted heteroaryl group having 5 to 20 ring-forming atoms, with the proviso that an anthracenyl group, carbazolyl group, azacarbazolyl group, benzimidazolyl group, dibenzofuryl group, and dibenzothienyl group are excluded;

$Ar^2$ is hydrogen atom, a substituted or unsubstituted aryl group having 6 to 20 ring-forming carbon atoms, or a substituted or unsubstituted heteroaryl group having 5 to 20 ring-forming atoms, with the proviso that an anthracenyl group is excluded;

n is an integer of 0 to 4, and, when n is 0, $L^1$ is not a single bond and $Ar^1$ is not hydrogen atom, and, when n is an integer of 2 to 4, $Ar^2$ groups and $L^2$ groups may be the same or different, respectively;

Z is $-L^3-Ar^3$;

$L^3$ is a substituted or unsubstituted arylene group having 6 to 20 ring-forming carbon atoms, with the proviso that a substituted or unsubstituted anthracenylene group and a substituted or unsubstituted fluorenylene group are excluded;

$Ar^3$ is a substituted or unsubstituted aryl group having 6 to 20 ring-forming carbon atoms or a substituted or unsubstituted heteroaryl group having 6 to 20 ring-forming atoms, with the proviso that an anthracenyl group, carbazolyl group, azacarbazolyl group, benzimidazolyl group, dibenzofuryl group, and dibenzothienyl group are excluded;

wherein at least one of $Ar^1$ to $Ar^3$ is a monovalent group which is formed from any of:

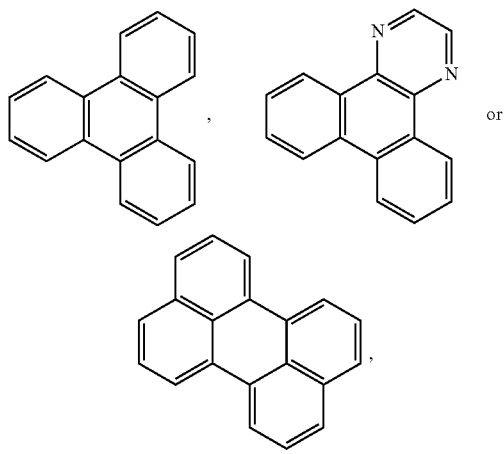

by removing a hydrogen atom from a ring carbon,
$L^1$ and $L^2$ cannot be a single bond at the same time, and $Ar^1$ and $Ar^2$ cannot be a hydrogen atom at the same time.

2. The organic electroluminescence device according to claim 1, wherein the nitrogen-comprising heterocyclic derivative is represented by formula (1b):

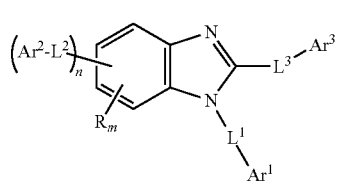

(1b)

wherein R, m, $L^1$, $L^2$, $L^3$, $Ar^1$, $Ar^2$, $Ar^3$, and n are as defined above.

3. The organic electroluminescence device according to claim 2, wherein the nitrogen-comprising heterocyclic derivative is represented by formula (3b):

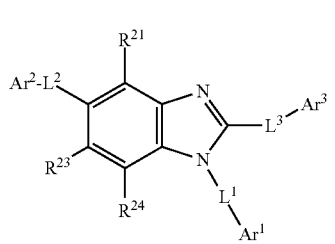

(3b)

wherein $L^1$ to $L^3$ and $Ar^1$ to $Ar^3$ are as defined above, and $R^{21}$, $R^{23}$ and $R^{24}$ are the same as R of formula (1).

4. The organic electroluminescence device according to claim 2, wherein the nitrogen-comprising heterocyclic derivative is represented by formula (4b):

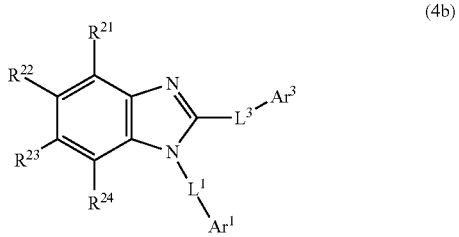

(4b)

wherein $L^1$, $L^3$, $Ar^1$ and $Ar^3$ are as defined above, and $R^{21}$ to $R^{24}$ are the same as R of formula (1).

5. The organic electroluminescence device according to claim 2, wherein the nitrogen-comprising heterocyclic derivative is represented by formula (5b):

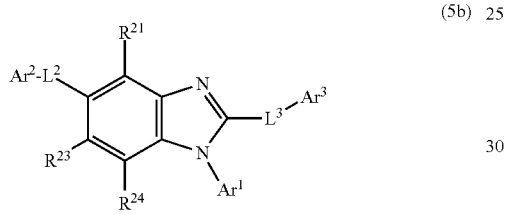

(5b)

wherein $L^2$, $L^3$, and $Ar^1$ to $Ar^3$ are as defined above, and $R^{21}$, $R^{23}$ and $R^{24}$ are the same as R of formula (1).

6. The organic electroluminescene device according to claim 2, represented by formula (2b):

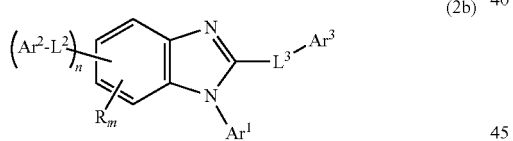

(2b)

wherein R, m, $L^2$, $L^3$, $Ar^1$, $Ar^2$, $Ar^3$, and n are as defined above.

7. The organic electroluminescence device according to claim 1, wherein the nitrogen-comprising heterocyclic derivative is an electron injecting material or an electron transporting material.

8. The organic electroluminescence device according to claim 1, wherein the nitrogen-comprising heterocyclic derivative is a light emitting material.

9. The organic electroluminescence device according to claim 1, wherein the light emitting layer comprises the nitrogen-comprising heterocyclic derivative.

10. The organic electroluminescence device according to claim 1, wherein the organic thin-film layer further comprises an electron injecting layer or an electron transporting layer, and the electron injecting layer or the electron transporting layer comprises the nitrogen-comprising heterocyclic derivative.

11. The organic electroluminescence device according to claim 10, wherein the electron injecting layer or the electron transporting layer further comprises a reducing dopant.

12. The organic electroluminescence device according to claim 11, wherein the reducing dopant is at least one substance selected from the group consisting of an alkali metal, an alkaline earth metal, a rare earth metal, an alkali metal oxide, an alkali metal halide, an alkaline earth metal oxide, an alkaline earth metal halide, a rare earth metal oxide, a rare earth metal halide, an organic complex of alkali metal, an organic complex of alkaline earth metal, and an organic complex of rare earth metal.

13. The organic electroluminescence device according to claim 1, wherein $Ar^1$ is a monovalent group which is formed from any of:

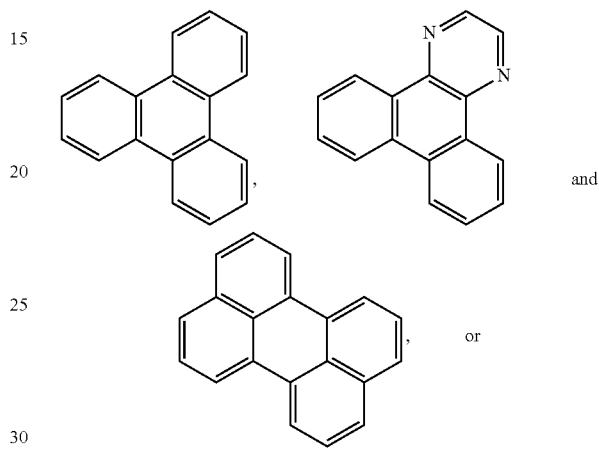

by removing a hydrogen atom from a ring carbon.

14. The organic electroluminescence device according to claim 1, wherein at least one of $Ar^1$ to $Ar^3$ is a monovalent group which is formed from any of:

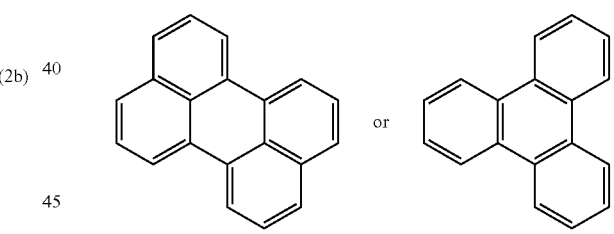

by removing a hydrogen atom from a ring carbon.

15. The organic electroluminescence device according to claim 1, wherein $Ar^1$ is a monovalent group which is formed from any of:

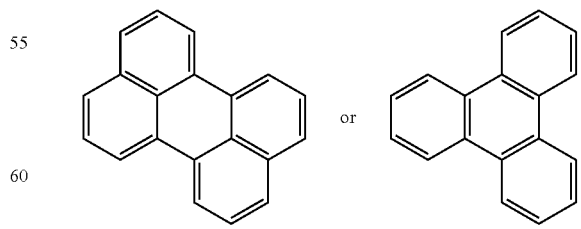

by removing a hydrogen atom from a ring carbon.

16. The organic electroluminescence device according to claim 1, wherein the derivative is represented by any of the following formulae: